US009765299B2

(12) United States Patent
Palecek et al.

(10) Patent No.: US 9,765,299 B2
(45) Date of Patent: Sep. 19, 2017

(54) CHEMICALLY DEFINED ALBUMIN-FREE CONDITIONS FOR CARDIOMYOCYTE DIFFERENTIATION OF HUMAN PLURIPOTENT STEM CELLS

(71) Applicant: Wisconsin Alumni Research Foundation, Madison, WI (US)

(72) Inventors: Sean Paul Palecek, Verona, WI (US); Xiaojun Lian, Madison, WI (US); Xiaoping Bao, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 14/850,451

(22) Filed: Sep. 10, 2015

(65) Prior Publication Data
US 2016/0068814 A1  Mar. 10, 2016

Related U.S. Application Data

(60) Provisional application No. 62/048,547, filed on Sep. 10, 2014.

(51) Int. Cl.
C12N 5/00 (2006.01)
C12N 5/077 (2010.01)

(52) U.S. Cl.
CPC ........ *C12N 5/0657* (2013.01); *C12N 2500/05* (2013.01); *C12N 2500/46* (2013.01); *C12N 2500/92* (2013.01); *C12N 2501/392* (2013.01); *C12N 2501/415* (2013.01); *C12N 2506/02* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 7,425,448 | B2 | 9/2008 | Xu |
| 7,763,464 | B2 | 7/2010 | Xu |
| 7,897,389 | B2 | 3/2011 | Gold |
| 8,158,421 | B2 | 4/2012 | Passier |
| 8,951,798 | B2 | 2/2015 | Palecek |
| 9,234,176 | B2 | 1/2016 | Wu |
| 2002/0076747 | A1 | 6/2002 | Price |
| 2008/0254003 | A1 | 10/2008 | Passier |
| 2011/0097799 | A1 | 4/2011 | Stankewicz |
| 2011/0142935 | A1 | 6/2011 | Kamp |
| 2012/0129211 | A1 | 5/2012 | Kattman |

FOREIGN PATENT DOCUMENTS

| | | |
|---|---|---|
| WO | 2008094597 A2 | 8/2008 |
| WO | 2010101849 A1 | 9/2010 |
| WO | 2011160128 A2 | 12/2011 |

OTHER PUBLICATIONS

Lian et al. Nat Protocol 2013;8:162-75.*
Usta et al. Ann Translat Med 2014;2-97:1-9.*
Wadhwa et al. Cloning Stem Cells 2009;11:387-95.*
Anton, Roman et al, ".beta.-Catenin signaling contributes to sternness and regulates early differentiation in murine embryonic stem cells", FEBS Lett., Oct. 15, 2007, vol. 581, No. 27, pp. 5247-5254.
Baba, Yoshihiro et al., "Constitutively Active .beta.-Catenin Confers Multilineage Differentiation Potential on Lymphoid and Myeloid Progenitors" , Immunity, Dec. 2005, vol. 23, No. 6, pp. 599-609.
Burridge et al., "A Universal System for Highly Efficient Cardiac Differentiation of Human Induced Pluripotent Stem Cells That Eliminates Interline Variability", PLoS One (Apr. 2011), 6(4):e18293.
Burridge et al., "Improved Human Embryonic Stem Cell Embryoid Body Homogeneity and Cardiomyocyte Differentiation from a Novel V-96 Plate Aggregation System Highlights Interline Variability", Stem Cells (Apr. 2007), 25:929-938.
Burridge et al., "Production of De Novo Cardiomyocytes: Human Pluripotent Stem Cell Differentiation and Direct Reprogramming", Cell Stem Cell (Jan. 2012), 10(1):16-28.
Chen, Baozhi et al., "Small molecule-mediated disruption of Wnt-dependent signaling in tissue regeneration and cancer", Nat. Chem. Biol., Feb. 2009, vol. 5, No. 2, pp. 100-107.
Claassen, David A., Michelle M. Desler, and Angie Rizzino. "ROCK inhibition enhances the recovery and growth of cryopreserved human embryonic stem cells and human induced pluripotent stem cells." Molecular reproduction and development 76.8 (Aug. 2009): 722-732.
Davidson, Kathryn et al., "Wnt/.beta.-catenin signaling promotes differentiation, not self-renewal, of human embryonic stem cells and is repressed by Oct. 4", PNAS, Mar. 20, 2012, vol. 109, No. 12, 4485-4490.
Franco, Diego et al., "Myosin light chain 2a and 2v identifies the embryonic outflow tract myocardium in the developing rodent heart", Anat. Rec., Jan. 1999, vol. 254, pp. 135-146.
Gonzalez, Rodolfo et al., "Stepwise Chemically Induced Cardiomyocyte Specification of Human Embryonic Stem Cells", Angew. Chem. Int. Ed. Oct. 2011, 50, 11181-11185.
Graichen, et al., "Enhanced cardiomyogenesis of human embryonic stem cells by a small molecular inhibitor of p38 MAPK." Differentiation (Apr. 2008), 76:357-370.
Gurney et al., "Wnt pathway inhibition via the targeting of Frizzled receptors results in decreased growth and tumorigenicity of human tumors", Proc. Natl. Acad. Sci. USA, Jul. 2012, vol. 109, No. 29, pp. 11717-11722.
Hagen et al., "Expression and Characterization of GSK-3 Mutants and Their Effect on .beta.-Catenin Phosphorylation in Intact Cells", J. Biol. Chem., Jun. 2002, vol. 26, pp. 23330-23335.
Hao et al., "In Vivo Structure-Activity Relationship Study of Dorsomorphin Analogues Identifies Selective VEGF and BMP Inhibitors", A.C.S. Chem. Biol., Feb. 2010, vol. 5, No. 2, pp. 245-253.

(Continued)

*Primary Examiner* — Janice Li
(74) *Attorney, Agent, or Firm* — Quarles & Brady LLP

(57) ABSTRACT

Methods for generating high-yield, high-purity cardiomyocyte progenitors or cardiomyocytes from pluripotent cells are described. Wnt/β-catenin signaling is first activated in pluripotent cells, by, for example, inhibiting Gsk-3 to obtain a first population of cells. Wnt/β-catenin signaling is then inhibited in the first cell population to induce cardiogenesis. One or more of these steps is performed under defined, albumin-free culture conditions.

20 Claims, 24 Drawing Sheets
(14 of 24 Drawing Sheet(s) Filed in Color)

(56) References Cited

OTHER PUBLICATIONS

He et al., "A Monoclonal Antibody against Wnt-1 Induces Apoptosis in Human Cancer Cells", Neoplasia, Jan./Feb. 2004, vol. 6, No. 1, pp. 7-14.
Honda et al., "Electrophysiological Characterization of Cardiomyocytes Derived From Human Induced Pluripotent Stem Cells", J Pharmacol Sci (Oct. 2011), 117:149-159.
Ieda et al., "Direct Reprogramming of Fibroblasts into Functional Cardiomyocytes by Defined Factors", Cell, Jul. 2010, vol. 142, No. 3, pp. 375-386.
Inman et al., "SB-431542 Is a Potent and Specific Inhibitor of Transforming Growth Factor-.beta. Superfamily Type I Activin Receptor-Like Kinase (ALK) Receptors ALK4, ALK5, and ALK7", Mol. Pharmacol., Jul. 2002, vol. 62, No. 1, pp. 65-74.
Johansson, Britt M., and Michael V. Wiles. "Evidence for involvement of activin A and bone morphogenetic protein 4 in mammalian mesoderm and hematopoietic development." Molecular and Cellular Biology 15.1 (Jan. 1995): 141-151.
Kattman, Steven J., et al. "Stage-specific optimization of activin/nodal and BMP signaling promotes cardiac differentiation of mouse and human pluripotent stem cell lines." Cell stem cell 8.2 (Feb. 2011): 228-240.
Kramer, Jan, et al. "Embryonic stem cell-derived chondrogenic differentiation in vitro: activation by BMP-2 and BMP-4." Mechanisms of development 92.2 (Apr. 2000): 193-205.
Kubalak et al., "Chamber specification of atrial myosin light chain-2 expression precedes septation during murine cardiogenesis", J. Biol. Chem., Jun. 1994, vol. 269, pp. 16961-16970.
Laflamme et al., "Cardiomyocytes derived from human embryonic stem cells in pro-survival factors enhance function of infarcted rat hearts", Nature Biotechnol (Sep. 2007), 25:1015-1024.
Lian, X. et al., "Directed cardiomyocyte differentiation from human pluripotent stem cells by modulating Wnt/[beta]-catenin signaling under fully defined conditions", Nature Protocols, Dec. 2012, vol. 8, No. 1, pp. 162-175.
Lian, X. et al., "Robust cardiomyocyte differentiation from human pluripotent stem cells via temporal modulation of canonical Wnt signaling," Proc. Natl. Acad. Sci., May 2012, 109:27, pp. E1848-E1857.
Matsui et al., "Induction of Initial Cardiomyocyte.sub.-Actin-Smooth Muscle-Actin—in Cultured Avian Pregastrula Epiblast: A Role for Nodal and BMP Antagonist", Dev. Dynam., Jun. 2005, vol. 233, No. 4, pp. 1419-1429.
Mummery, Christine, et al. "Differentiation of human embryonic stem cells to cardiomyocytes role of coculture with visceral endoderm-like cells." Circulation 107.21 (May 2003): 2733-2740.
Naito, Atsuhiko T., et al. "Developmental stage-specific biphasic roles of Wnt/β-catenin signaling in cardiomyogenesis and hematopoiesis." Proceedings of the National Academy of Sciences 103.52 (Dec. 2006): 19812-19817.
Nakajima et al., "Significance of Bone Morphogenetic Protein-4 Function in the Initial Myofibrillogenesis of Chick Cardiogenesis", Develop. Biol., May 2002, vol. 245, No. 2, pp. 291-303.
Nakanishi et al., "Directed induction of anterior and posterior primitive streak by Wnt from embryonic stem cells cultured in a chemically defined serum-free medium," The FASEB Journal, Research Communication, Jan. 2009, vol. 23, 114-122.
Paige, Sharon L., et al. "Endogenous Wnt/β-catenin signaling is required for cardiac differentiation in human embryonic stem cells." PloS one 5.6 (Jun. 2010): e11134.
Pucéat, Michel. "Protocols for cardiac differentiation of embryonic stem cells." Methods 45.2 (Jun. 2008): 168-171.
Qyang, et al., "The Renewal and Differentiation of Isl1+ Cardiovascular Progenitors Are Controlled by a Wnt/.beta.-Catenin Pathway," Cell Stem Cell, Aug. 2007, 1, 165-179.
Ren et al., "Small molecule Wnt inhibitors enhance the efficiency of BMP-4-directed cardiac differentiation of human pluripotent stem cells", J. Mol. Cell. Cardiol., Sep. 2011, vol. 51, No. 3, pp. 280-287.
Ruzicka and Schwartz, "Sequential activation of alpha-actin genes during avian cardiogenesis: vascular smooth muscle alpha-actin gene transcripts mark the onset of cardiomyocyte differentiation", J. Cell Biol., Dec. 1988, vol. 107, pp. 2575-2586.
Schuldiner, Maya, et al. "Effects of eight growth factors on the differentiation of cells derived from human embryonic stem cells." Proceedings of the National Academy of Sciences 97.21 (Oct. 2000): 11307-11312.
Segev et al., "Molecular analysis of cardiomyocytes derived from human embryonic stem cells", Dev. Growth Differ., Jun. 2005, vol. 47, pp. 295-306.
Shiraki, Nobuaki, et al., "Differentiation of mouse and human embryonic stem cells into hepatic lineages." Genes to cells 13.7 (Jul. 2008): 731-746.
Sugi and Lough, "Onset of Expression and Regional Deposition of Alpha-Smooth and Sarcomeric Actin During Avian Heart Development", Dev. Dyn., Feb. 1992, vol. 193, pp. 116-124.
Tohyama, Shugo, et al. "Distinct Metabolic Flow Enables Large-Scale Purification of Pluripotent Stem Cell-Derived Cardiomyocytes." Circulation 124.21 (Nov. 2011): A12671.
Tran et al., "Wnt3a-Induced Mesoderm Formation and Cardiomyogenesis in Human Embryonic Stem Cells", Stem Cells, Aug. 2009, vol. 27, No. 8, pp. 1869-1878.
Wang et al, "Cardiac Induction of Embryonic Stem Cells by a Small Molecule Inhibitor of Wnt/.beta.-Catenin Signaling", A.C.S. Chem. Biol., Feb. 2011, vol. 6, No. 2, pp. 192-107.
Watanabe et al., "A ROCK inhibitor permits survival of dissociated human embryonic stem cells", Nat Biotechnol (Jun. 2007), 25(6):681-686.
Willems et al., "Small-Molecule Inhibitors of the Wnt Pathway Potently Promote Cardiomyocytes From Human Embryonic Stem Cell-Derived Mesoderm", Circ. Res., Jul. 2011, vol. 109, No. 4, pp. 360-364.
Wobus, A. M., R. Grosse, and J. Schöneich. "Specific effects of nerve growth factor on the differentiation pattern of mouse embryonic stem cells in vitro." Biomedica biochimica acta 47.12 (1988): 965-973.
Wobus, Anna M., et al. "Retinoic acid accelerates embryonic stem cell-derived cardiac differentiation and enhances development of ventricular cardiomyocytes." Journal of molecular and cellular cardiology 29.6 (Jun. 1997): 1525-1539.
Xu, Chunhui, et al. "Characterization and enrichment of cardiomyocytes derived from human embryonic stem cells." Circulation research 91.6 (online Aug. 2002): 501-508.
Yang, Lei, et al. "Human cardiovascular progenitor cells develop from a KDR+ embryonic-stem-cell-derived population." Nature 453.7194 (Feb. 2008): 524-528.
Zhang, et al., "Direct differentiation of atrial and ventricular myocytes from human embryonic stem cells by alternating retinoid signals," Cell Research (online Nov. 2010) 21:579-587.

\* cited by examiner

Components of the media used in Example 1.

| Components | B27-ins | 5F | 4F | 3F | 3-Se | 3-Pu | 3-Pr | Se | Pu | Pr |
|---|---|---|---|---|---|---|---|---|---|---|
| RPMI | ✓ | ✓ | ✓ | ✓ | ✓ | ✓ | ✓ | ✓ | ✓ | ✓ |
| Biotin | ✓ | | | | | | | | | |
| DL α-tocopherol Acetate | ✓ | | | | | | | | | |
| DL α-tocopherol | ✓ | | | | | | | | | |
| Vitamin A (acetate) | ✓ | | | | | | | | | |
| BSA | ✓ | ✓ | ✓ | | | | | | | |
| Catalase | ✓ | | | | | | | | | |
| Human Transferrin | ✓ | ✓ | | | | | | | | |
| Superoxide Dismutase | ✓ | | | | | | | | | |
| Corticosterone | ✓ | | | | | | | | | |
| D-Galactose | ✓ | | | | | | | | | |
| Ethanolamine HCL | ✓ | | | | | | | | | |
| Glutathione (reduced) | ✓ | | | | | | | | | |
| L-Carnitine HCl | ✓ | | | | | | | | | |
| Linoleic Acid | ✓ | | | | | | | | | |
| Linolenic Acid | ✓ | | | | | | | | | |
| Progesterone | ✓ | ✓ | ✓ | ✓ | ✓ | ✓ | | | | ✓ |
| Putrescine 2HCl | ✓ | ✓ | ✓ | ✓ | ✓ | | ✓ | | ✓ | |
| Sodium Selenite | ✓ | ✓ | ✓ | ✓ | | ✓ | ✓ | ✓ | | |
| T3(triodo-I-thyronine) | ✓ | | | | | | | | | |

Fig. 9

CHEMICALLY DEFINED ALBUMIN-FREE CONDITIONS FOR CARDIOMYOCYTE DIFFERENTIATION OF HUMAN PLURIPOTENT STEM CELLS

CROSS-REFERENCE TO RELATED APPLICATIONS

This application claims the benefit of U.S. provisional Application No. 62/048,547 filed on Sep. 10, 2014, which is incorporated by reference herein in its entirety.

STATEMENT REGARDING FEDERALLY SPONSORED RESEARCH OR DEVELOPMENT

This invention was made with government support under EB007534 awarded by the National Institutes of Health. The government has certain rights in the invention.

BACKGROUND

Generating cardiovascular cells from pluripotent stem cells holds great promise for cardiovascular research and therapy. The past 10 years have seen rapid methodological advances for creating de novo human cardiomyocytes. In particular, the ability of human pluripotent stem cells (hPSCs) to differentiate to cells in cardiac lineages has attracted significant interest, with a strong focus on applications in modeling cardiovascular development, drug discovery, safety pharmacology and cell therapy in myocardial infarction and heart failure.

Several efficient differentiation strategies involving stage-specific activation and inhibition of different signaling pathways, with the goal of mimicking in vivo cardiac development, have been devised to generate cardiomyocytes from hPSCs (see, e.g., Yang, L. et al. Human cardiovascular progenitor cells develop from a KDR+ embryonic-stem-cell-derived population. *Nature* 453, 524-8 (2008); Kattman, S. J. et al. Stage-specific optimization of activin/nodal and BMP signaling promotes cardiac differentiation of mouse and human pluripotent stem cell lines. *Cell Stem Cell* 8, 228-40 (2011); Laflamme, M. A. et al. Cardiomyocytes derived from human embryonic stem cells in pro-survival factors enhance function of infarcted rat hearts. *Nat. Biotechnol.* 25, 1015-24 (2007); Burridge, P. W. et al. A universal system for highly efficient cardiac differentiation of human induced pluripotent stem cells that eliminates interline variability. *PLoS One* 6, e18293 (2011); and Mummery, C. et al. Differentiation of human embryonic stem cells to cardiomyocytes: role of coculture with visceral endoderm-like cells. *Circulation* 107, 2733-40 (2003)). However, most of these approaches are not chemically-defined, contain xenogenic components, or require expensive recombinant proteins, limiting their application for large-scale cardiomyocyte production for therapeutic applications.

Previously, we disclosed the Gsk3 inhibitor/Wnt inhibitor (GiWi) method for robust hPSC differentiation to cardiomyocytes under serum-free and growth factor-free conditions (see U.S. Patent Publication No. 2013/0189785, which is incorporated by reference herein). In one embodiment, this GiWi method applies two small molecules, a Gsk3 inhibitor and a Porcupine inhibitor, at precise developmental stages to sequentially promote mesoderm formation and then cardiomyocyte specification (Lian, X. et al. Directed cardiomyocyte differentiation from human pluripotent stem cells by modulating Wnt/β-catenin signaling under fully defined conditions. *Nat. Protoc.* 8, 162-75 (2013); Lian, X. J. et al. Robust cardiomyocyte differentiation from human pluripotent stem cells via temporal modulation of canonical Wnt signaling. *Proc. Natl. Acad. Sci. U.S.A.* 109, E1848-E1857 (2012)). Although the RPMI/B27-ins (B27 without insulin) medium used in the GiWi protocol lacks animal sera and growth factors, the inclusion of bovine serum albumin (BSA) increases the cost and adds xenogenic components, limiting the protocol's potential for large-scale cardiomyocyte production. Furthermore, the use of BSA in the GiWi protocol may decrease differentiation consistency, because of the substantial batch-to-batch variability of the albumin used in the protocol.

Despite these known disadvantages of using albumin in protocols for differentiating human pluripotent stem cells to cardiomyocytes, albumin is an essential ingredient in all previously disclosed protocols. In some protocols, the BSA is replaced with a recombinant albumin, such as recombinant human albumin (see, e.g., U.S. Patent Publication No. 2014/0134733). Although the use of recombinant albumin may address some of the issues associated by the use of albumin in differentiation protocols (e.g., the need for batch-to-batch consistency resulting from impurities in animal-derived albumin), it is substantially more costly than BSA, and its use would be prohibitively expensive for a commercially viable protocol optimized for large-scale cardiomyocyte production.

Accordingly, there is a need in the art for a cardiac differentiation protocol that uses defined culture conditions in the absence of albumin or other substances previously thought to be an essential part of such protocols to produce cardiomyocyte progenitors and cardiomyocytes from hPSCs in a more efficient, cost-effective manner.

BRIEF SUMMARY

The invention relates generally to methods for cardiac induction in hPSCs and, more particularly, to methods for generating, from hPSCs, populations of cardiomyocyte progenitors that go on to become functional cardiomyocytes by sequential activation and inhibition of Wnt/β-catenin signaling under chemically-defined, albumin-free conditions.

Accordingly, in a first aspect, the disclosure encompasses a method for generating a population of cardiomyocyte progenitors from pluripotent stem cells, comprising: (i) activating Wnt/β-catenin signaling in cultured pluripotent stem cells (e.g., primate pluripotent stem cells, human pluripotent stem cells, or non-human primate pluripotent stem cells) to obtain a first cell population; and (ii) inhibiting Wnt/β-catenin signaling in the cultured first cell population after the culturing period in step (i) to obtain a second cell population comprising cardiomyocyte progenitors. The step of activating Wnt/β-catenin signaling, the step of inhibiting Wnt/β-catenin signaling, or both occur under albumin-free culturing conditions.

In some embodiments, the step of activating Wnt/β-catenin signaling occurs by inhibiting Gsk3 in the pluripotent stem cells. In some embodiments, Gsk3 in the pluripotent stem cells is inhibited by contacting the pluripotent stem cells with a small molecule that inhibits Gsk3. In some embodiments, the small molecule inhibitor that inhibits Gsk3 is CHIR 99021, CHIR 98014, BIO-acetoxime, BIO, LiCl, SB 216763, SB 415286, AR A014418, 1-Azakenpaullone, Bis-7-indolylmaleimide, or a combination thereof. In some embodiments, the small molecule Gsk3 inhibitor is CHIR 99021, CHIR 98014, or BIO-acetoxime. In some such embodiments, the small molecule Gsk3 inhibitor is present in a concentration of from 0.2 to 9 µM. In some embodiments, the small molecule Gsk3 inhibitor is CHIR 99021.

In some embodiments, the step of inhibiting Gsk3 in the pluripotent stem cells is performed by RNA interference knockdown of Gsk3. In other embodiments, the step of inhibiting Gsk3 in the pluripotent stem cells is performed by overexpressing a dominant negative form of Gsk3.

In yet other embodiments, the Wnt/β-catenin pathway signaling is activated in the cultured pluripotent stem cells by overexpressing β-catenin in the cultured pluripotent stem cells.

In some embodiments, the step of inhibiting Wnt/β-catenin signaling in the first cell population includes contacting the first cell population with a small molecule that inhibits Wnt/β-catenin signaling. In some embodiments, the small molecule that inhibits Wnt/β catenin signaling is a small molecule that stabilizes axin and stimulates β-catenin degradation. In some such embodiments, the small molecule that stabilizes axin and stimulates β-catenin degradation include 3,5,7,8-Tetrahydro-2-[4-(trifluoromethyl)phenyl]-4H-thiopyrano[4,3-d]pyrimidin-4-one ("XAV939") and/or 4-(1,3,3a,4,7,7a-hexahydro-1,3-dioxo-4,7-methano-2H-isoindol-2-yl)-N-8-quinolinyl-benzamide ("IWR-1").

In other embodiments, the small molecule that inhibits Wnt/β catenin signaling is a small molecule that prevents palmitylation of Wnt proteins by porcupine (i.e., a porcupine inhibitor). In some embodiments, the small molecule that prevents palmitylation of Wnt proteins by porcupine includes N-(6-Methyl-2-benzothiazolyl)-2-[(3,4,6,7-tetrahydro-4-oxo-3-phenylthieno[3,2-d]pyrimidin-2-yl)thio]-acetamide ("IWP2"), 2-(3,4,6,7-tetrahydro-3-(2-methoxyphenyl)-4-oxothieno[3,2-d]pyrimidin-2-ylthio)-N-(6-methylbenzo[d]thiazol-2-yl)acetamide ("IWP4"), 4-(2-Methyl-4-pyridinyl)-N-[4-(3-pyridinyl)phenyl]benzeneacetamide ("Wnt-C59"), or a combination thereof. In some such embodiments, the porcupine inhibitor is present in a concentration of from 0.2 to 5 µM In yet another embodiment, the small molecule that inhibits Wnt/β catenin signaling is a small molecule that increases the activity level of casein kinase 1α. In some embodiments, the small molecule that increases the activity level of casein kinase 1α is 6-(Di methylamino)-2-[2-(2,5-dimethyl-1-phenyl-1H-pyrrol-3-yl)ethenyl]-1-methyl-4,4-methylenebis[3-hydroxy-2-naphthalenecarboxylate] (2:1)-quinolinium, or a combination thereof.

In further embodiments, inhibiting the Wnt/β-catenin signaling in the first cell population includes contacting the first cell population with at least one antibody that blocks activation of a Wnt ligand receptor. In some embodiments, the at least one antibody binds to one or more Wnt ligand family members. In other embodiments, the at least one antibody binds to the Wnt ligand receptor.

In other embodiments, inhibiting the Wnt/β-catenin signaling in the first cell population comprises reducing β-catenin expression in the first cell population. In some embodiments, reducing β-catenin expression comprises expressing shRNA for β-catenin in the first cell population. In some embodiments, reducing β-catenin expression comprises overexpressing Axin2 in the first cell population.

In further embodiments of the above-mentioned method, the pluripotent stem cells in step (i), the first cell population in step (ii), or both are cultured under conditions that, in addition to being albumin-free, are also free of one or more of L-ascorbic acid 2-phosphate, transferrin, sodium selenite, progesterone, and putrescine.

In some embodiments, the second cell population is cultured for a period after ending the inhibition of Wnt/β-catenin signaling initiated in step (iii) to obtain a cell population comprising cardiomyocytes.

In some embodiments, the step of inhibiting Wnt/β-catenin signaling in the first cell population is performed immediately after the step of activating Wnt/β-catenin signaling in the pluripotent stem cells is completed.

In some embodiments, the second cell population is cultured for a period after ending the inhibition of Wnt/β-catenin signaling initiated in step (iii) to obtain a cell population comprising cardiomyocytes.

In some embodiments, where a cell population comprising cardiomyocytes is obtained, at least 85% of the cells in the cell population are cardiac troponinT (cTnT)-positive, and the cell population comprising the at least 85% cTnT-positive cells is obtained without the use of a cell separation step on the second cell population.

In a second aspect, the disclosure encompasses a method for culturing pluripotent stem cells to obtain a population of cardiomyocytes, the method comprising the steps of: sequentially inhibiting Gsk3 in the pluripotent cells and then inhibiting Wnt signaling in the Gsk3 inhibited cells under albumin-free conditions; and culturing the sequentially inhibited cells in an albumin-free culture medium to form a differentiated cell population comprising cardiomyocytes.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

FIG. 1A is a schematic of the protocol for differentiation of hPSCs to cardiomyocytes via treatment with Wnt-modulating small molecules in serum-free medium.

FIG. 1B shows purity, determined by flow cytometry analysis of cTnT expression of cardiomyocytes differentiated from ES03 hESCs in RPMI basal medium supplemented with the indicated components. 5F: transferrin, sodium selenite, progesterone, putrescine, BSA; 4F: sodium selenite, progesterone, putrescine, BSA; 3F: sodium selenite, progesterone, putrescine. #P<0.005, indicated medium versus 3F with 12 µM CH; Student's t test.

FIG. 1C is a Western blot analysis of brachyury expression in ES03 hESCs treated with indicated concentrations of CH in albumin-free or albumin-containing RPMI medium for 24 hours.

FIG. 1D shows immunolabeling for brachyury expression in hPSCs treated with 6 µM CH in albumin-free or albumin-containing RPMI for 24 hours. BSA: bovine serum albumin; HRA: human recombinant albumin. Scale bar, 50 µm.

FIG. 1E is a flow cytometry analysis of cTnT expression in cardiomyocytes differentiated from human 19-9-11 iPSCs in RPMI.

FIG. 1F shows immunolabeling for cTnT expression in cardiomyocytes differentiated from human 19-9-11 iPSCs in RPMI. Scale bar, 100 µm.

FIG. 1G shows coimmunolabeling of cTnI and α-actinin in a single 19-9-11 iPSC-derived cardiomyocyte. Scale bar, 10 µm.

FIG. 1H shows coimmunolabeling of cTnT and CX43 in 19-9-11 iPSC derived cardiomyocytes. Scale bar, 10 µm.

FIG. 1I shows a typical action potential of an individual ES03 hESC-derived cardiomyocyte recorded via patch clamp. The lower inset shows enlarged waveform of a single action potential. Dashed line indicates resting potential 0 mV.

FIG. 7A shows coimmunolabeling of α-actinin and connexin-43 in 19-9-11 iPSC-derived cardiomyocytes. FIG. 7B shows immunolabeling of cTnT in 19-9-11iPSC-derived cardiomyocytes. Scale bars, 50 µm.

FIG. 9 shows components of the media used in Example 1.

Figure 1A:
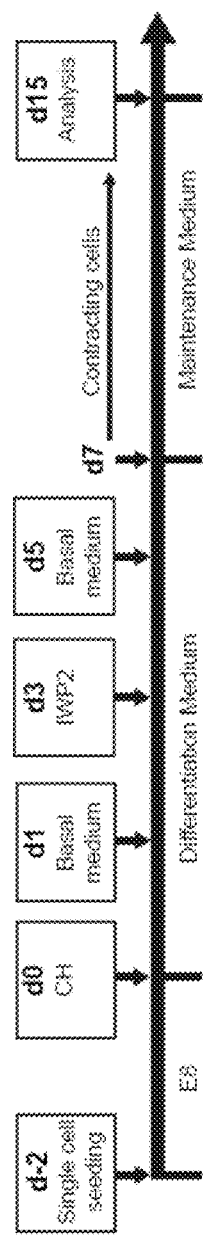
FIGS. 1A-I show that albumin is not required for hPSC differentiation to cardiomyocytes.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In describing the embodiments and claiming the invention, the following terminology will be used in accordance with the definitions set out below.

As used herein, "about" means within 5% of a stated concentration range or within 5% of a stated time frame.

The terms "defined culture medium," "defined medium," and the like, as used herein, indicate that the identity and quantity of each medium ingredient is known.

As used herein, the terms "chemically-defined culture conditions," "fully defined, growth factor free culture conditions," and "fully-defined conditions" indicate that the identity and quantity of each medium ingredient is known and the identity and quantity of supportive surface is known.

As used herein, the term "albumin-free conditions" indicates that the culture medium used contains no added albumin in any form, including without limitation Bovine Serum Albumin (BSA) or any form of recombinant albumin.

As used herein, "effective amount" means an amount of an agent sufficient to evoke a specified cellular effect according to the present invention.

As used herein, the term "Gsk 3 inhibited cells" refers to (i) cells in which Gsk3 has previously been inhibited, but in which Gsk3 is no longer actively inhibited; or (ii) cells in which Gsk3 is not being actively inhibited, but for which a parental stem cell or progenitor cell population had had Gsk3 inhibited. Within the context of the present disclosure such "Gsk 3 inhibited cells" correspond to some embodiments in which a first cell population (comprising mesendodermal markers) is obtained after exposing human pluripotent stem cells to a Gsk3 inhibitor for a defined period of time, after which Gsk-3 is no longer actively inhibited.

As used herein, the term "pluripotent cell" means a cell capable of differentiating into cells of all three germ layers. Examples of pluripotent cells include embryonic stem cells and induced pluripotent stem (iPS) cells. As used herein, "iPS cells" refer to cells that are substantially genetically identical to their respective differentiated somatic cell of origin and display characteristics similar to higher potency cells, such as ES cells, as described herein. The cells can be obtained by reprogramming non-pluripotent (e.g., multipotent or somatic) cells.

As used herein, "iPS cell derivation" means reprogramming a somatic cell to become pluripotent.

The present invention involves a method for differentiating hPSCs under albumin-free conditions to obtain a population of cardiomyocyte progenitors, the method including the steps of: sequentially activating Wnt/β-catenin pathway signaling in pluripotent stem cells under albumin-free conditions to obtain a first cell population characterized by a majority of cells expressing mesodermal or endodermal markers ("mesendoderm" markers). Subsequently, Wnt/β-catenin pathway signaling in the first population of cells is inhibited under albumin-free conditions for a period of time, and then relieved of Wnt/β-catenin pathway signaling to differentiate the first population of cells into a second cell population containing cardiomyocyte progenitors. In some embodiments, the second cell population, comprising cardiomyocyte progenitors, is then further cultured for a period of time to obtain a population of cells comprising cardiomyocytes.

The methods have valuable applications such as inexpensive and reproducible generation of human cardiomyocyte progenitors or cardiomyocytes. Generating cardiomyocyte progenitors or cardiomyocytes in completely chemically-defined, xeno-free conditions will facilitate translation of these cells to regenerative therapies.

As disclosed herein, in some embodiments of the differentiation methods, exogenous TGF superfamily growth factors are not required to generate cardiomyocyte progenitors or cardiomyocytes from pluripotent cells.

As shown herein, in some cases, albumin-free directed differentiation, including temporal modulation of Wnt pathway regulators as set forth herein, can generate more than 90% cTnT+ cardiomyocytes from pluripotent stem cells.

As described in further detail below, the inventors' simplified albumin-free protocols target key regulatory elements of the Wnt/β-catenin signaling pathway, simplifying the steps and components involved in deriving cardiomyocyte progenitors and cardiomyocytes from pluripotent stem cells.

Timing

In some embodiments, in the first step, i.e., step (i) of the just-mentioned method, pluripotent stem cells to be differentiated are subjected to activation of Wnt/β-catenin pathway signaling for a period of about 8 hours to about 48 hours, e.g., about 8 hours, 12 hours, 16 hours, 20 hours, 24 hours, 28 hours, 32 hours, 36 hours, 40 hours, 44 hours, 48 hours, or another period of Wnt/β-catenin pathway signaling activation from about 8 hours to about 48 hours to obtain a first cell population of cells, characterized by the expression of mesendodermal markers. In one embodiment, pluripotent stem cells are subjected to Wnt/β-catenin pathway signaling activation for a period of about 24 hours.

In some embodiments, after the end of the Wnt/β-catenin pathway activation step of step (i), i.e., after the agent for activating the Wnt/β-catenin pathway signaling has been removed or has ended, the first population of cells is optionally cultured in the absence of external Wnt/β-catenin pathway activation for a period of at least about 8 hours to about 60 hours, e.g., about 10 hours, 11 hours, 12 hours, 14 hours, 16 hours, 20 hours, 24 hours, 30 hours, 36 hours, 40 hours, 44 hours, 48 hours, 52 hours, 56 hours, 60 hours or another period from at least about 8 hours to about 60 hours. In one embodiment, this culture period is about 12 hours. In another embodiment, this culture period is about 48 hours.

In some embodiments, no such intermediate step is performed. Instead, immediately after step (i), the first population is subjected to inhibition of Wnt/β-catenin pathway signaling. In some embodiments, step (ii) is initiated at least about 33 hours to about 74 hours following the beginning of step (i), e.g., at least about 34 hours, 36 hours, 38 hours, 39 hours, 40 hours, 45 hours, 50 hours, 60 hours, 65 hours, 68 hours, 69 hours, 70 hours, 72 hours, or another time point from at least about 33 hours to about 74 hours following the beginning of step (i). In some embodiments, step (ii) is initiated 36 hours after the beginning of step (i). In other embodiments, step (ii) begins 72 hours after the beginning of step (i).

In some embodiments, the medium from the optional intermediate step is only partially replaced with fresh medium to obtain a "combined medium" in which the first cell population is cultured at the beginning of step (ii). In some embodiments, the proportion of fresh medium in the final culture medium volume at the beginning of step (ii) ranges from about 30% to about 70%, e.g., about 35%, 40%, 45%, 50%, 55%, 60%, 65% or another proportion from about 30% to about 70%. In some embodiments, the proportion of fresh medium in the final culture volume at the beginning of step (ii) is about 50%. In other embodiments, the medium from the optional intermediate step is completely replaced with fresh medium at the beginning of step (ii).

In one embodiment, where β-catenin RNA interference is to be used to inhibit the Wnt/β-catenin signaling pathway, RNA interference is initiated about 36 hours following the beginning of Gsk3 inhibition. In another embodiment, where small molecule-mediated inhibition of the Wnt/β-catenin signaling pathway is to be used, the first cell population is contacted with the small molecule inhibitor at about 3 days following Gsk3 inhibition.

Typically, inhibition of Wnt/β-catenin signaling in the first population of cells during step (ii) is maintained for a period of at least about 1 day to about 6 days, e.g., about 1 day, 2 days, 2.5 days, 3 days, 3.5 days, 4 days, 5 days, or another period of Wnt/β-catenin signaling inhibition from at least about 1.5 days to about 6 days. In some embodiments, where a small molecule inhibitor is used to inhibit Wnt/β-catenin signaling, the first cell population is contacted with the small molecule for a period of about 2 days, and then culture of the first cell population continues in the substantial absence of the small molecule inhibitor. In other embodiments, where inducible RNA interference is used (e.g., with an inducing agent such as doxycycline to drive expression of tet-on expression cassette) to knockdown expression of β-catenin, induction and maintenance of β-catenin is for a period of about 3.5 days, after which induction of β-catenin shRNA expression is terminated, and then culture of the first cell population continues in the substantial absence of the inducing agent.

While, in some cases, cells are cultured continuously from the beginning of step (i) to step (ii) to obtain a population comprising cardiomyocyte progenitors, in other cases cultured cells are removed from a culture substrate and frozen for storage thus allowing for the differentiation method to be resumed after thawing cells at a later date. For example, in some cases, the first population of cells obtained after step (i) is collected and stored frozen in any number of suitable cell cryopreservation media known in the art, and then later thawed and cultured to resume the differentiation method starting at the optional intermediate step and/or continuing to step (ii) in which Wnt/β-catenin pathway signaling is inhibited to drive differentiation into a second cell population comprising cardiomyocytes.

In other embodiments, the second population of cells, comprising cardiomyocyte progenitors, is cryopreserved, and thawed at a later date for continued culture of the second population in order to obtain a population comprising cardiomyocytes. Accordingly, one of ordinary skill in the art will appreciate that, where the differentiation methods described herein include a cell freezing step, the absolute time interval between at least two steps will be different from the corresponding step interval in embodiments that do not include a freezing step.

Typically, the second cell population obtained by the disclosed methods comprises a very high proportion of cardiomyocyte progenitors. In some embodiments, the second cell population comprises about 50% to about 99% cardiomyocyte progenitors, e.g., about 52%, 55% 67%, 70%, 72%, 75%, 80%, 85%, 90%, 95%, 98%, or another percent of cardiomyocyte progenitors from about 50% to about 99% cardiomyocyte progenitors.

In some embodiments, after ending the inhibition of Wnt/β-catenin signaling initiated during step (ii), as described herein, the resulting second population of cells, comprising cardiomyocyte progenitors, is cultured for an additional period of time to obtain a cell population comprising cardiomyocytes. In some embodiments, the additional cell culture period for the second cell population ranges from at least about 20 days to about 200 days, e.g, about 23 days, 25 days, 27 days, 30 days, 35 days, 40 days, 45 days, 55 days, 70 days, 90 days, 100 days, 120 days. 150 days, 170 days, 180 days, 190 days, or another culture period, after ending inhibition of Wnt/β-catenin signaling, from at least about 20 days to about 200 days following the end of Wnt/β-catenin signaling inhibition. In one embodiment, the second population of cells is cultured for a period of at least about 25 days after ending inhibition of Wnt/β-catenin signaling.

In some embodiments, continued culture of the second population (in the absence of Wnt/β-catenin signaling inhibition) yields a cell population comprising about 50% to about 99% cardiomyocytes, e.g., about 52%, 55% 67%, 70%, 72%, 75%, 80%, 85%, 90%, 95%, 98%, or another percent of cardiomyocytes from about 50% to about 99% cardiomyocytes.

In some embodiments, no cell separation step or method is used to obtain a second cell population comprising at least 70% cTnT-positive cells or at least 85% cTnT-positive cells. In other embodiments, cell separation or enrichment methods, e.g., FACS, MACS, metabolic selection of cardiomyocytes, or laser-targeted ablation of non-cardiomyotcyes are used to obtain a second cell population further enriched in cardiomyocytes relative to the second cell population prior to application of a cell separation or enrichment method. Cardiomyocytes are identified by the presence of one or more cardiomyocyte markers (e.g., cTnT expression) or functional characteristics (e.g., spontaneous contractility).

Useful gene expression or protein markers for identifying cardiomyocyte progenitors or cardiomyocytes, include, but are not limited to, Smooth Muscle Actin, Cardiac Troponin T, light meromyosin MF20, sarcomeric myosin, Myosin Light Chain ventricular, Myosin Light Chain Atrial, and alphaα-actinin, NKX2.5, TBX5, GATA4, MEF2, and combinations thereof. Such markers can be detected at the mRNA expression level or protein level by standard methods in the art.

In some embodiments, where cardiomyocytes are to be generated, certain cardiomyocyte functional criteria are also assessed. Such functional cardiomyocyte criteria include, but are not limited to, spontaneous contractility, response to electrical pacing, the presence of organized contractile structures, or a combination thereof.

Pluripotent stem cells (PSCs) suitable for the differentiation methods disclosed herein include, but are not limited to, human embryonic stem cells (hESCs), human induced pluripotent stem cells (hiPSCs), non-human primate embryonic stem cells (nhpESCs), non-human primate induced pluripotent stem cells (nhpiPSCs).

Activation of Wnt/β-Catenin Signaling

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, activation of Wnt/β-catenin signaling is achieved by inhibition of Gsk3 phosphotransferase activity or Gsk3 binding interactions. While not wishing to be bound by theory, it is believed that inhibition of Gsk3 phosphorylation of β-catenin will inhibit tonic degradation of β-catenin and thereby increase β-catenin's level and activity to drive differentiation of pluripotent stem cells to an endodermal/mesodermal lineage. Gsk3 inhibition can be achieved in a variety of ways including, but not limited to, providing small molecules that inhibit Gsk3 phosphotransferase activity, RNA interference knockdown of Gsk3, and overexpression of dominant negative form of Gsk3. Dominant negative forms of Gsk3 are known in the art as described, e.g., in Hagen, T. et al. Expression and characterization of GSK-3 mutants and their effect on beta-catenin phosphorylation in intact cells. *J Biol Chem*, 277, 23330-5 (2002), which describes a Gsk3 comprising a R96A mutation.

In some embodiments, the Wnt/β-catenin signaling pathway is activated by inhibiting Gsk3 in pluripotent stem cells by contacting the pluripotent stem cells with a small molecule that inhibits Gsk3 phosophotransferase activity or Gsk3 binding interactions. Suitable small molecule Gsk3 inhibitors include, but are not limited to, CHIR 99021, CHIR 98014, BIO-acetoxime, BIO, LiCl, SB 216763, SB 415286, AR A014418, 1-Azakenpaullone, Bis-7-indolylmaleimide, and any combinations thereof. In some embodiments, any of CHIR 99021, CHIR 98014, and BIO-acetoxime are used to inhibit Gsk3 in pluripotent stem cells in the differentiation methods described herein. In one embodiment, the small molecule Gsk3 inhibitor to be used is CHIR99021 at a concentration ranging from about 3 μM to about 9 μM, e.g., about 3 μM, 4 μM, 5 μM, 6 μM, 7 μM, 8 μM, 9 μM or another concentration of CHIR99021 from about 3 μM to about 9 μM. In another embodiment, the small molecule Gsk3 inhibitor to be used is CHIR 98014 at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of CHIR-98014 from about 0.1 μM to about 1 μM. In another embodiment, the small molecule Gsk3 inhibitor to be used is BIO-acetoxime at a concentration ranging from about 0.1 μM to about 1 μM, e.g., about 0.1 μM, 0.2 μM, 0.3 μM, 0.4 μM, 0.5 μM, 0.6 μM, 0.7 μM, 0.8 μM, 0.9 μM or another concentration of BIO-acetoxime from about 0.1 μM to about 1 μM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β siRNA (catalog #6301 from Cell Signaling Techology®, Danvers, Mass.), or a retroviral vector with an inducible expression cassette for Gsk3, e.g., a commercially available Tet-inducible retroviral RNAi system from Clontech (Mountainview, Calif.) Catalog No. 630926, or a cumate-inducible system from Systems Biosciences, Inc. (Mountainview, Calif.), e.g., the SparQ® system, catalog no.

QM200PA-2. In other embodiments, the Wnt/β-catenin signaling pathway is activated by overexpressing β-catenin itself, e.g., human β-catenin (GenBank Accession Nos: X87838 and CAA61107.1 for nucleotide and protein sequences, respectively). In one embodiment, β-catenin overexpression is inducible β-catenin overexpression achieved using, e.g., any of the just-mentioned inducible expression systems. Alternatively, a constitutively active, stabilized isoform of β-catenin is used, which contains point mutations S33A, S37A, T41A, and S45A as described, e.g., in Baba, Y. et al. Constitutively active β-catenin confers multi-lineage differentiation potential on lymphoid and myeloid progenitors. *Immunity* 23, 599-609 (2005).

In yet other embodiments, Wnt/β-catenin signaling pathway activation in pluripotent stem cell is achieved by contacting the cells with an agent that disrupts the interaction of β-catenin with Axin, a member of the β-catenin destruction complex. Disruption of Axin-β-catenin interaction allows β-catenin to escape degradation though the destruction complex thereby increasing the net level of β-catenin to drive β-catenin signaling. For example, the Axin-β-catenin interaction can be disrupted in pluripotent cells by contacting them with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD4 Biosciences. An effective concentration of SKL2001 to activate Wnt/β-Catenin signaling ranges from about 10 μM to about 100 μM, about 20 μM, 30 μM, 40 μM, 50 μM, 60 μM, 70 μM, 80 μM, 90 μM or another concentration of SKL2001 from about 10 μM to about 100 μM.

Inhibition of Wnt/β-Catenin Signaling

Inhibition of Wnt/β-catenin pathway signaling means inhibition of TCF/LEF-β-catenin mediated gene transcription. Inhibition of Wnt/β-catenin pathway signaling can be achieved in a variety of ways including, but not limited to: providing small molecule inhibitors, RNA interference of, or blocking antibodies against functional canonical Wnt ligands or Wnt pathway receptors (e.g., Frizzled and LRPS/6); providing small molecules that promote degradation of β-catenin and/or TCF/LEF; gene interference knockdown of β-catenin and/or TCF/LEF; overexpression of a dominant negative form of β-catenin lacking the sequence for binding to TCF/LEF; overexpressing Axin2 (which increases β-catenin degradation); providing a small molecule inhibitor of a TCF/LEF and β-catenin interaction; and providing a small molecule inhibitor of a TCF/LEF-β-catenin and DNA promoter sequence interaction.

In some cases, inhibition of Wnt/β-catenin pathway signaling in a first cell population is achieved by contacting the first cell population with one or more small molecule inhibitors of a Wnt ligand (e.g., a small molecule that inhibits secretion of the Wnt ligand) or inhibit Wnt ligands and their corresponding receptors interaction. Suitable small molecule inhibitors include, but are not limited to, 4-(2-Methyl-4-pyridinyl)-N-[4-(3-pyridinyl)phenyl]benzeneacetamide ("Wnt-059") available commercially, e.g. as Tocris catalog no. 5148, N-(6-Methyl-2-benzothiazolyl)-2-[(3,4,6,7-tetrahydro-4-oxo-3-phenylthieno[3,2-d]pyrimidin-2-yl)thio]-acetamide ("IWP2") available commercially, e.g., as Sigma catalog no. IO536; 2-(3,4,6,7-tetrahydro-3-(2-methoxyphenyl)-4-oxothieno[3,2-d]pyrimidin-2-ylthio)-N-(6-methylbenzo[d]thiazol-2-yl)acetamide ("IWP4") available commercially, e.g., as catalog no. 04-00306 from Stemgent (San Diego, Calif.); 4-(1,3,3a,4,7,7a-Hexahydro-1,3-dioxo-4,7-methano-2H-isoindol-2-yl)-N-8-quinolinyl-Benzamide ("IWR-1") available commercially, e.g., as Sigma catalog no. 10161; Benzoic acid, 2-phenoxy-, 2-[(5-methyl-2-furanyl) methylene] hydrazide ("PNU-74654"), e.g., Sigma catalog no. P0052; or a combination thereof.

In some embodiments, the first population of cells is contacted with one or more small molecule compounds that promote degradation of β-catenin. In some cases, such small molecule compounds are compounds that, directly or indirectly, stabilize Axin, which is a member of the β-catenin destruction complex, and thereby enhance degradation of β-catenin. Examples of Axin-stabilizing compounds include, but are not limited to, 3,5,7,8-Tetrahydro-2-[4-(trifluoromethyl)phenyl]-4H-thiopyrano[4,3-d]pyrimidin-4-one ("XAV939"), e.g., Sigma catalog no. X3004; 4-(1,3,3a,4,7,7a-Hexahydro-1,3-dioxo-4,7-methano-2H-isoindol-2-yl)-N-8-quinolinyl-Benzamide ("IWR-1") available commercially, e.g., as Sigma catalog no. 10161. In some cases, such small molecule compounds are compounds that, directly or indirectly, activate casein kinase 1α (CK1), which is a member of the β-catenin destruction complex, and thereby enhance degradation of β-catenin. Examples of CK1-stabilizing compounds include, but are not limited to, 6-(Dimethylamino)-2-[2-(2,5-dimethyl-1-phenyl-1H-pyrrol-3-yl)ethenyl]-1-methyl-4,4-methylenebis[3-hydroxy-2-naphthalenecarboxylate] (2:1)-quinolinium ("Pyrvinium pamoate salt hydrate"), e.g., Sigma catalog no. P0027.

A suitable working concentration range for such small molecule inhibitors is from about 0.1 μM to about 100 μM, e.g., about 2 μM, 5 μM, 7 μM, 10 μM, 12 μM, 15 μM, 18 μM, or another working concentration of one or more the foregoing small molecule inhibitors ranging from about 0.1 μM to about 100 μM. In one embodiment, IWP2 or IWP4 or Wnt-059 are used at a working concentration of from about 1 to 4 μM. In another embodiment, IWP2 or IWP4 or Wnt-059 are used at a working concentration of about 2.5 μM. In other embodiments, the above-mentioned small molecule inhibitors are used at the corresponding target $IC_{50}$.

In other embodiments, inhibition of Wnt/β-catenin pathway signaling in the first cell population is enabled by RNA interference to decrease the expression of one or more targets in the Wnt/β-catenin pathway. For example in some cases, RNA interference is against β-catenin itself. In one embodiment, where one or more short hairpin interfering RNAs (shRNAs) are to be used to knock down β-catenin expression, at least one of the following shRNA sequences are used: (SEQ ID NO:1) 5'-CCGGAGGTGCTATCTGTCT-GCTCTACTCGAGTAGAGCAGACAGATAGCAC-CTTTTT T-3' or
(SEQ ID NO:2) 5'-CCGGGCTTGGAATGAGACTGCT-GATCTCGAGATCAGCAGTCTCATT CCAAGCTTTTT-3'. Such shRNAs may be transfected as synthetic shRNAs into the first cell population by a number of standard methods known in the art. Alternatively, shRNA sequences may be expressed from an expression vector, e.g., from a plasmid expression vector, a recombinant retrovirus, or a recombinant lentivirus.

In some embodiments, the first cell population is generated from a genetically modified pluripotent stem cell line comprising an inducible expression cassette for expression of an interfering RNA, e.g., an shRNA against β-catenin, as exemplified herein. The use of an inducible expression cassette allows temporal control of β-catenin knockdown. Such temporal control is well suited to the timing of Wnt/β-catenin signaling inhibition used in the differentiation methods described herein.

As an alternative method for inhibiting Wnt/β-catenin signaling in the first cell population, the first cell population is contacted with at least one antibody that blocks activation of a Wnt ligand receptor. In some embodiments, the at least one antibody binds to one or more Wnt ligand family members and inhibits binding of the one or more Wnt ligands to their receptors. Such antibodies are known in the art, e.g., an anti-Wnt-β antibody as described in He, B. et al. A monoclonal antibody against Wnt-β induces apoptosis in human cancer cells. *Neoplasia* 6, 7-14 (2004). In other embodiments, the blocking antibody is targeted against a Wnt ligand receptor and blocks the interaction of Wnt ligands with the receptor, as described, e.g., in Gurney, A. et al. Wnt pathway inhibition via the targeting of Frizzled receptors results in decreased growth and tumorigenicity of human tumors. *Proc. Natl. Acad. Sci. USA* 109, 11717-22 (2012).

Culture Media

Defined media and substrate conditions for culturing pluripotent stem cells, as used in the methods described herein, are well known in the art. The media used herein are limited only in that they are albumin-free. In some exemplary embodiments, pluripotent stem cells to be differentiated according to the methods disclosed herein are cultured in an albumi-free medium on a Matrigel substrate (BD Biosciences, NJ) or Synthemax surfaces (Corning) according to the manufacturer's protocol or on a Corning® Synthemax surface.

Upon initiating the first step and throughout the differentiation methods provided herein, pluripotent cells are typically cultured in a medium substantially free of insulin. In one embodiment, the medium used for differentiation method comprises the following components: 0.1 mg/ml Apo-transferrin, 30 μM Sodium selenite, 0.02 μg/ml Progesterone, and 16 mg/ml Putrescine. In some embodiments, the cell culture media used for the differentiation methods described herein are substantially free of one or more of these ingredients. In other embodiments, the medium used in the step (i) includes about 100 ng/ml Activin.

A number of known basal culture media are suitable for use throughout the differentiation methods described herein. Such basal cell culture media include, but are not limited to, RPMI, DMEM/F12 (1:3), DMEM/F12 (1:1), DMEM/F12 (3:1), F12, DMEM, and MEM. In some embodiments, these basal cell culture media are supplemented with 50 to 200 μg/ml L-Ascorbic acid 2-phosphate sesquimagnesium salt hydrate (e.g. Sigma, catalog no. A8960).

In another embodiment, the cell culture medium used is RPMI supplemented with L5. In yet another embodiment, the cell culture medium used is DMEM/F12 (1:3) supplemented with B27 (minus insulin).

The invention will be more fully understood upon consideration of the following non-limiting Examples. It is specifically contemplated that the methods disclosed are suited for pluripotent stem cells generally. All publications, patents, and patent applications disclosed herein are hereby incorporated by reference as if set forth in their entirety.

EXAMPLES

Example 1: Albumin-Free hPSC Differentiation to Cardiomyocytes

Abstract.

In this Example, we describe a minimum differentiation system that employs small molecules to modulate Wnt activity but lacks serum albumin, which negatively affects Gsk3 inhibitor activity. Using this simple, defined platform, we demonstrate efficient, robust, and cost-effective cardiomyocyte differentiation, an important step toward large scale production of human cardiomyocytes for research and clinical applications.

General Procedures and Results.

Bovine Serum Albumin (BSA) is present in the RPMI/B27-ins (B27 without insulin supplement) cardiac differentiation medium used in the GiWi method that we previously disclosed in U.S. Patent Publication No. 2013/0189785 (FIG. 1A). We have now simplified our GiWi protocol and developed an albumin-free cardiomyocyte differentiation platform.

First, we compared B27-ins with other published recipes for cardiomyocyte differentiation (Burridge, P. W. et al. A universal system for highly efficient cardiac differentiation of human induced pluripotent stem cells that eliminates interline variability. *PLoS One* 6, e18293 (2011); Uosaki, H. et al. Efficient and scalable purification of cardiomyocytes from human embryonic and induced pluripotent stem cells by VCAM1 surface expression. *PLoS One* 6, e23657 (2011); Minami, I. et al. A small molecule that promotes cardiac differentiation of human pluripotent stem cells under defined, cytokine- and xeno-free conditions. *Cell Rep.* 2, 1448-60 (2012); Hudson, J. et al. Primitive cardiac cells from human embryonic stem cells. J. *Stem Cells Dev.* 21, 1513-23 (2012); Xu, C. et al. Human embryonic stem cell-derived cardiomyocytes can be maintained in defined medium without serum. *Stem Cells Dev.* 15, 931-41 (2006); Burridge, P. et al. Production of de novo cardiomyocytes: human pluripotent stem cell differentiation and direct reprogramming. *Cell Stem Cell* 10, 16-28 (2012); Mummery, C. L. et al. Differentiation of Human ES and iPS Cells to Cardiomyocytes: A Methods Overview. *Circ. Res.* 111, 344-58 (2012); Passier, R. et al. Increased cardiomyocyte differentiation from human embryonic stem cells in serum-free cultures. *Stem Cells* 23, 772-80 (2005)). We identified five commonly-shared components (transferrin, sodium selenite, progesterone, putrescine, and BSA) in basal differentiation media. A summary of the components for the media discussed in this Example is shown in FIG. 9.

Figure 1B:
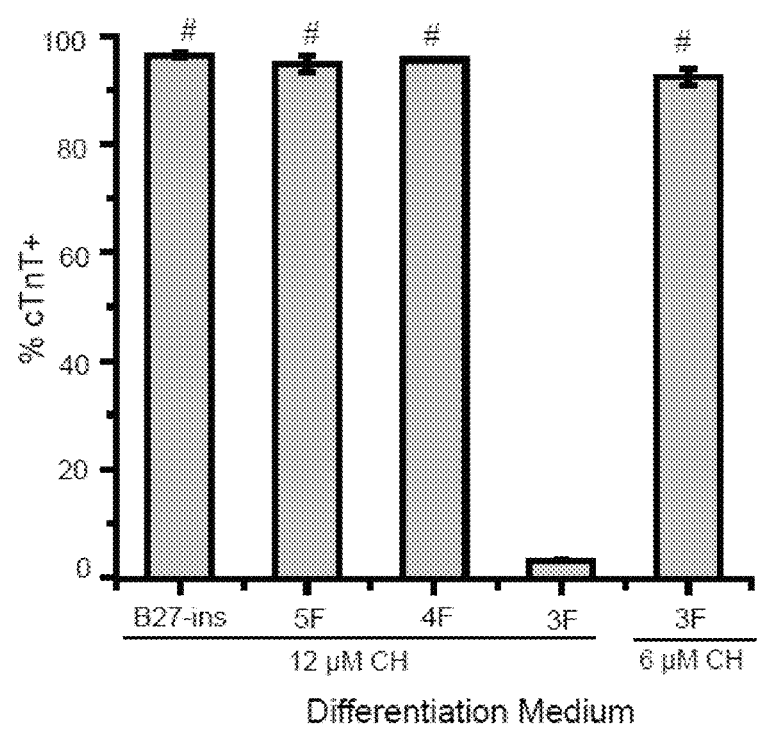

RPMI containing these five components (5F) supported hPSC differentiation to more than 90% cardiac troponin T (cTnT)-expressing cardiomyocytes, comparable to RPMI/B27-ins (FIG. 1B). In addition, removal of transferrin (4F) also produced 90% cTnT+ cells.

However, removal of BSA from the 4F system resulted in virtually no cardiomyocytes. Gsk3 inhibitor treatment, 12 μM CHIR99021 (CH) at day 0, caused prolific cell death by 24 hr in the absence of BSA.

Figure 2A:
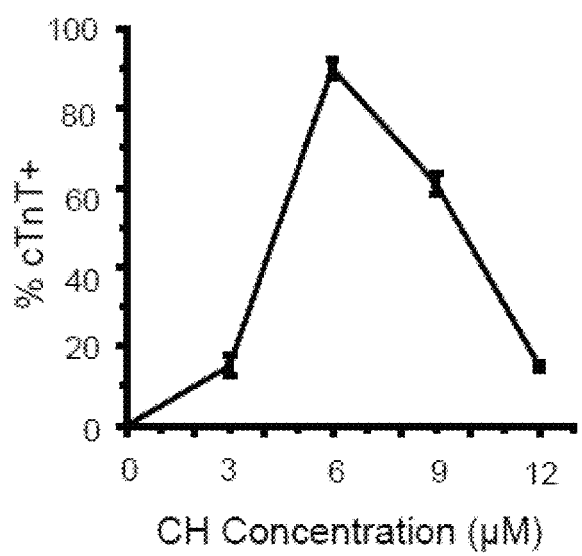
FIGS. 2A and 2B show purity of cardiomyocytes, determined by flow cytometric analysis of cTnT expression, differentiated from ES03 hESCs in albumin-free media with the indicated concentrations of CH (FIG. 2A) or the indicated concentration of IWP2 (FIG. 2B).
Figure 2B:
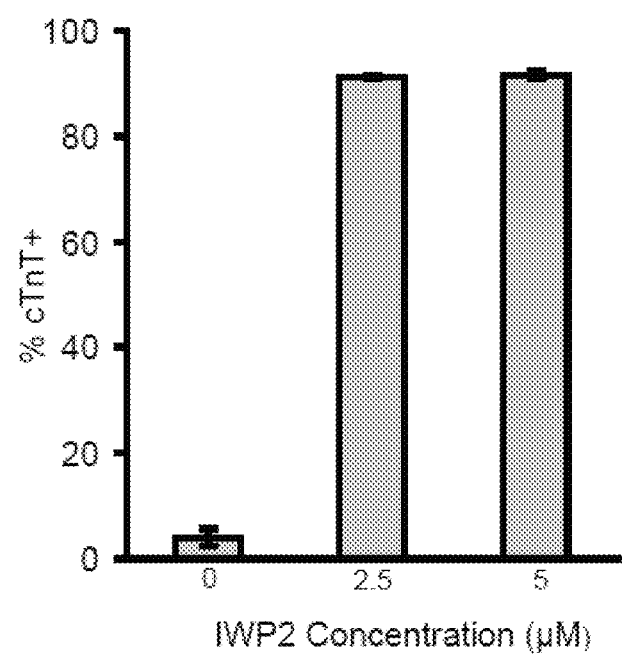

We then tuned the CH concentration in RPMI supplemented with 3 factors (sodium selenite, progesterone, putrescine). Surprisingly, 6 μM CH produced more than 90% cTnT+ cells in the absence of albumin (FIGS. 1B and 2A). In addition, we found that 2.5 μM IWP2 was sufficient to induce more than 90% cTnT+ cells (FIG. 2B), substantially lower than the 5 μM IWP2 required in the presence of BSA. These results demonstrate that albumin is not necessary for cardiomyocyte differentiation, and in fact its presence diminishes activity of small molecule agonists and antagonists of Wnt signaling.

Figure 2C:
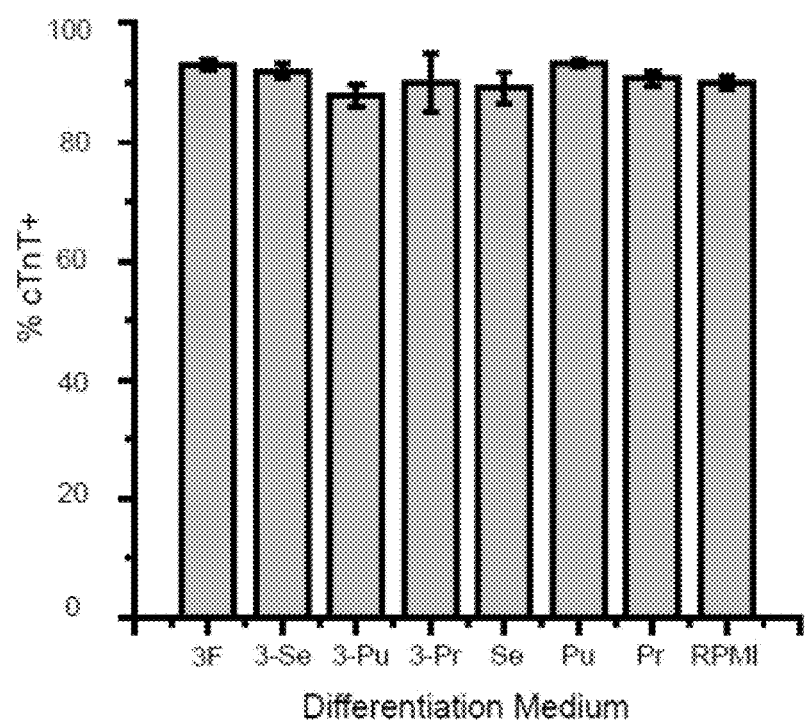
FIG. 2C shows purity of cardiomyocytes differentiated from ES03 hPSCs in RPMI medium supplemented with indicated components. 3F: sodium selenite, progesterone, putrescine; 3-Se: progesterone, putrescine; 3-Pu: sodium selenite, progesterone; 3-Pr: sodium selenite, putrescine; Se: sodium selenite; Pu: putrescine; Pr: progesterone.
Figure 2D:
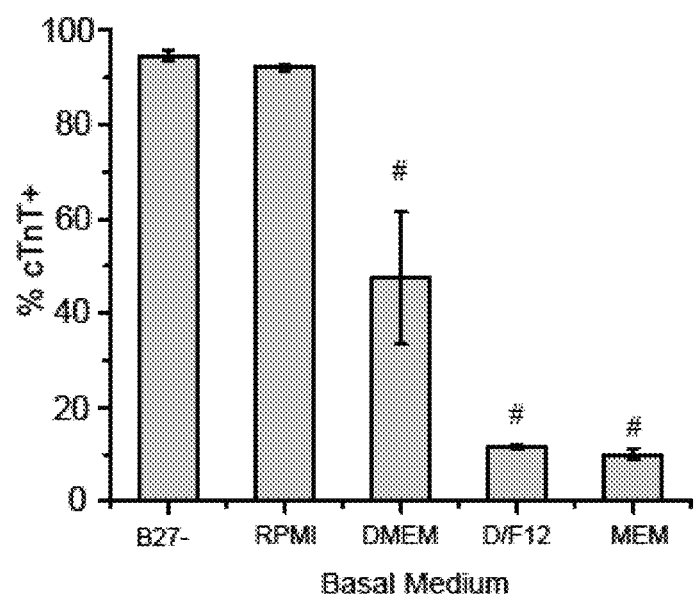
FIG. 2D shows purity of cardiomyocytes differentiated from ES03 hESCs in indicated basal media, B27-ins as a control. #P<0.005, other indicated basal medium versus RPMI; Student's t test. Three biological replicates were performed.

Removal of sodium selenite, progesterone and putrescine from 3F resulted in similar cardiomyocyte purity and yield (FIG. 2C). Thus, RPMI lacking supplements is sufficient to support hPSC differentiation to cardiomyocytes using the GiWi method. We then assessed the suitability of other common basal media in the GiWi protocol and found that DMEM, DMEM/F12 and MEM supported cardiomyocyte differentiation, but RPMI outperformed these media (FIG. 2D).

Figure 1C:
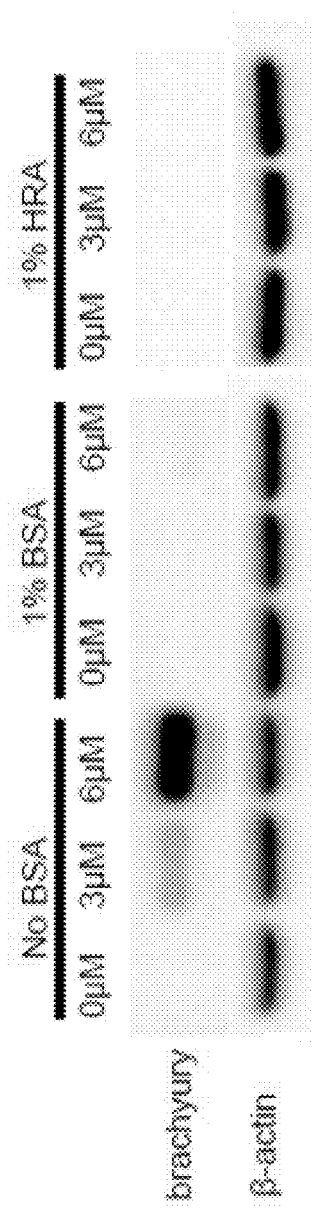
Figure 1D:
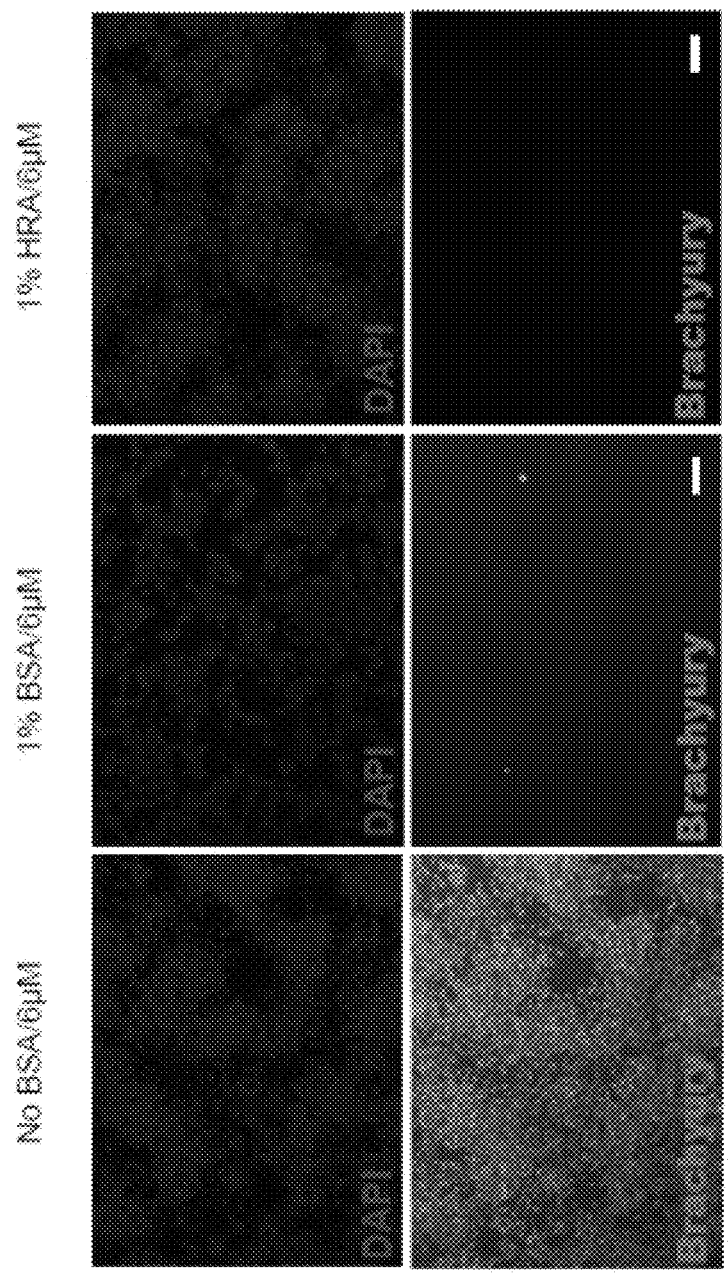

To confirm that 6 μM CH directed hPSCs to mesendoderm in the absence of BSA, we assessed the expression of brachyury following exposure to CH in the presence and absence of BSA. 6 µM CH in albumin-free RPMI induced robust brachyury expression after 24 hr as assessed by western blot and immunostaining. However, 1% BSA completely blocked brachyury expression at CH concentrations up to 6 µM (FIGS. 1C and 1D), demonstrating Wnt activation induced by Gsk3 inhibitor treatment is more efficient in media lacking albumin. CH concentrations up to 6 µM were also unable to induce brachyury expression in the presence of 1% human recombinant albumin (HRA) (FIGS. 1C and 1D). However, 30 µM CH induced brachyury expression in medium containing 1% HRA (FIGS. 1C and 1D).

We tested this albumin-free simplified GiWi protocol in multiple hESC (ES03, ES03-GFP, H9, HS181, H1) and iPSC (19-9-11, 6-9-9, IMR90C4, 19-9-7) lines. All lines produced 88-98% cTnT+ cells with yields of greater than $1\times10^6$ cardiomyocytes/cm$^2$ (Table 1). These cardiomyocytes exhibited spontaneous contraction for more than 8 months.

TABLE 1

Percent and yield of cTnT+ cardiomyocytes present at day 15

| Cell line | cTnT+ cells (%) | Number of cTnT+ cells ($10^6$/cm$^2$) |
| --- | --- | --- |
| ES03 | 97.2 ± 0.2 | 1.3 ± 0.2 |
| ES03-GFP | 92.5 ± 1.8 | 1.3 ± 0.1 |
| H1 | 88.7 ± 1.1 | 1.2 ± 0.1 |
| H9 | 90.6 ± 0.4 | 1.2 ± 0.2 |
| HS181 | 91.9 ± 1.2 | 1.0 ± 0.2 |
| 19-9-7 | 90.1 ± 1.0 | 1.2 ± 0.2 |
| 19-9-11 | 94.0 ± 2.6 | 1.3 ± 0.1 |
| 6-9-9 | 93.5 ± 2.9 | 1.0 ± 0.2 |
| IMR90C4 | 90.8 ± 0.8 | 1.1 ± 0.2 |

Data are presented as mean ± SD of three independent experiments.

Figure 1E:
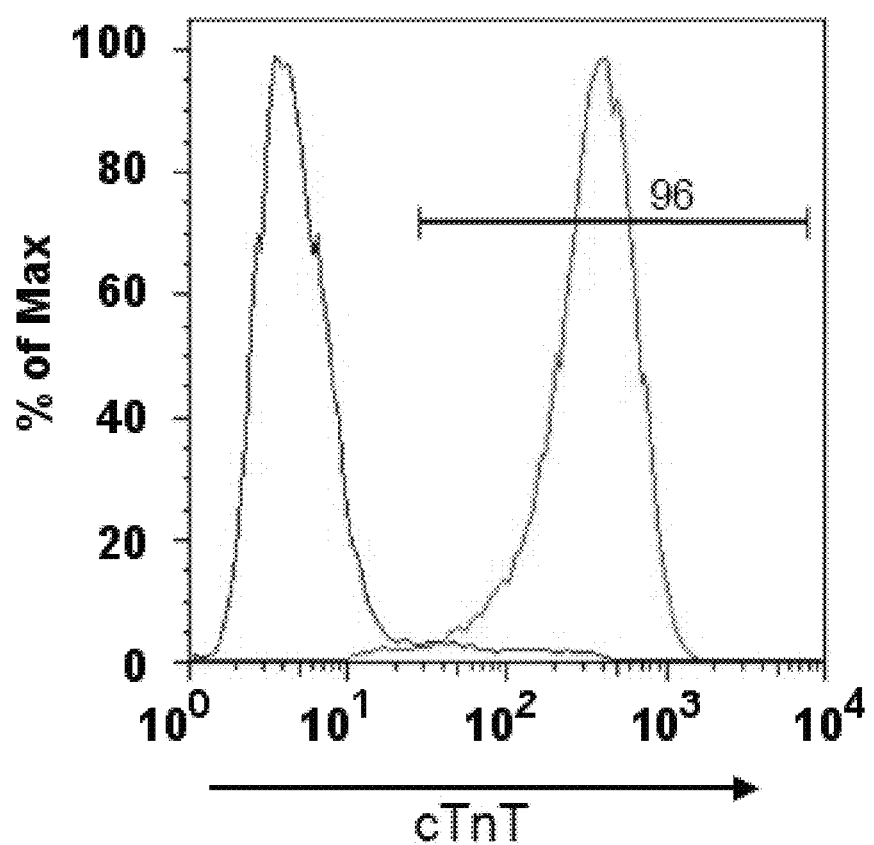
Figure 1F:
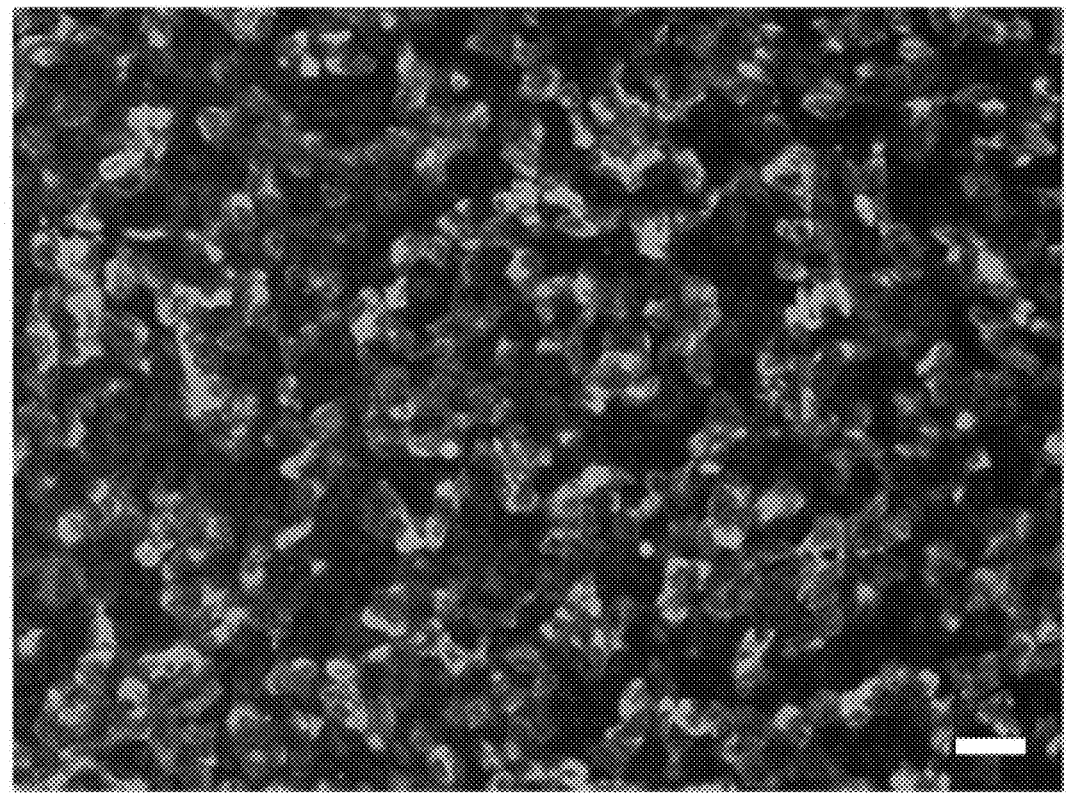
Figure 3A:
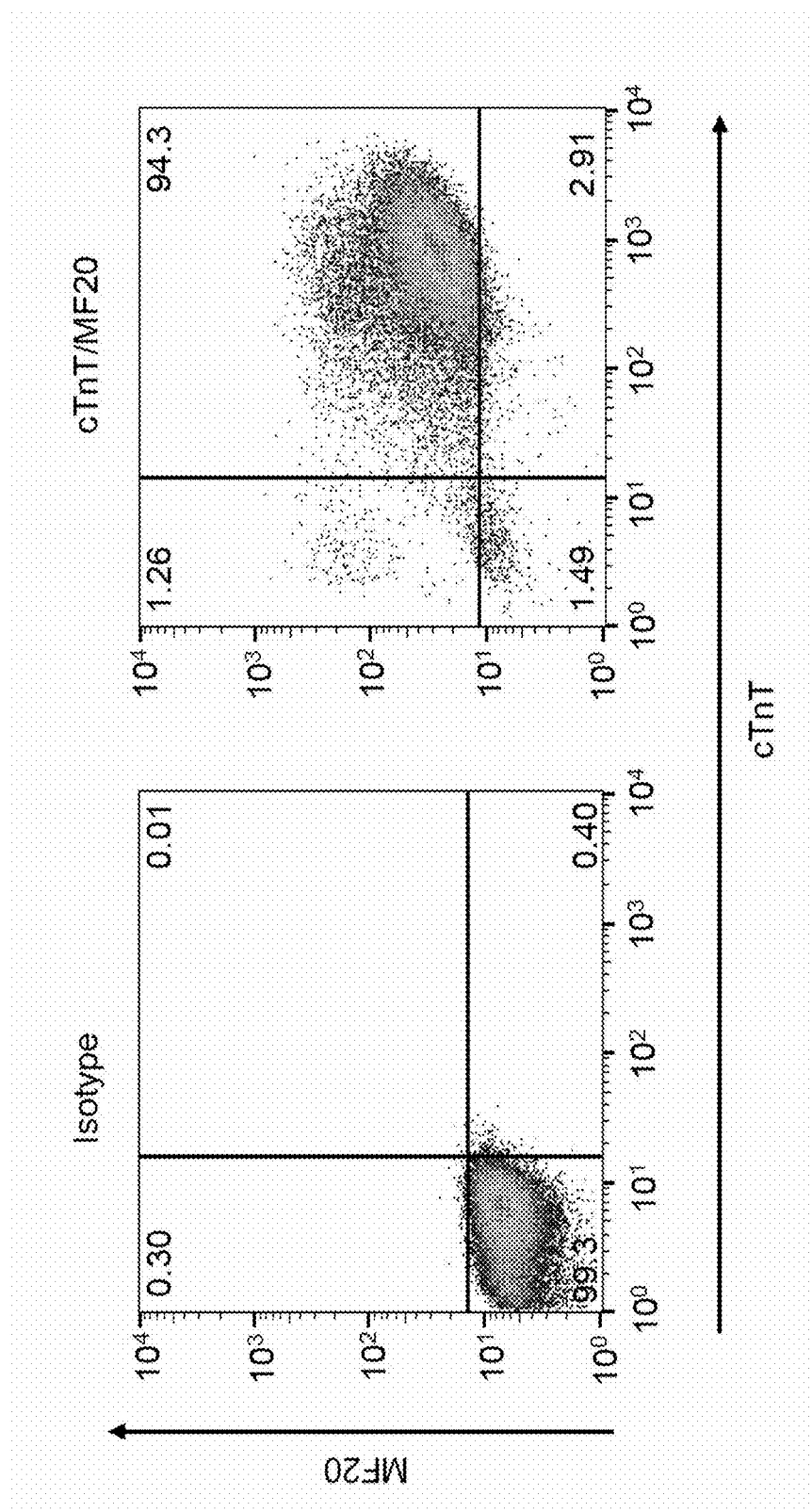
FIGS. 3A and 3B show purity of cardiomyocytes, determined by flow cytometric analysis of cTnT/MF20 (FIG. 3A) or α-actinin (FIG. 3B) expression, differentiated from ES03 hESCs in RPMI.
Figure 3B:
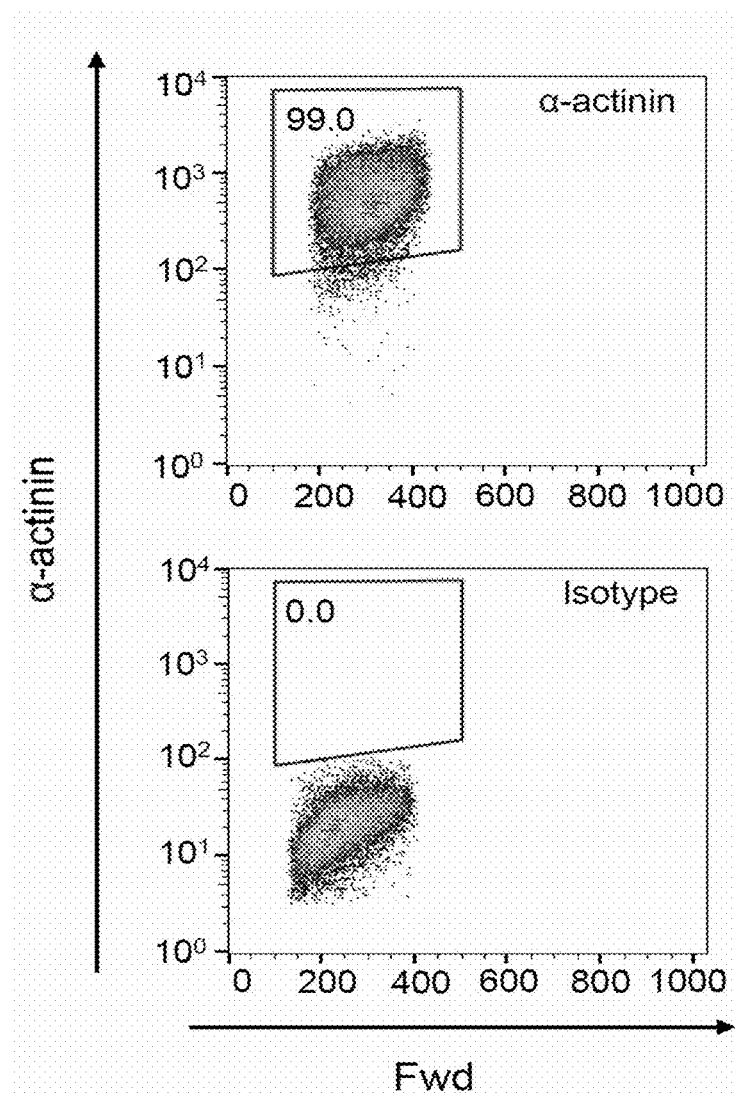
Figure 3C:
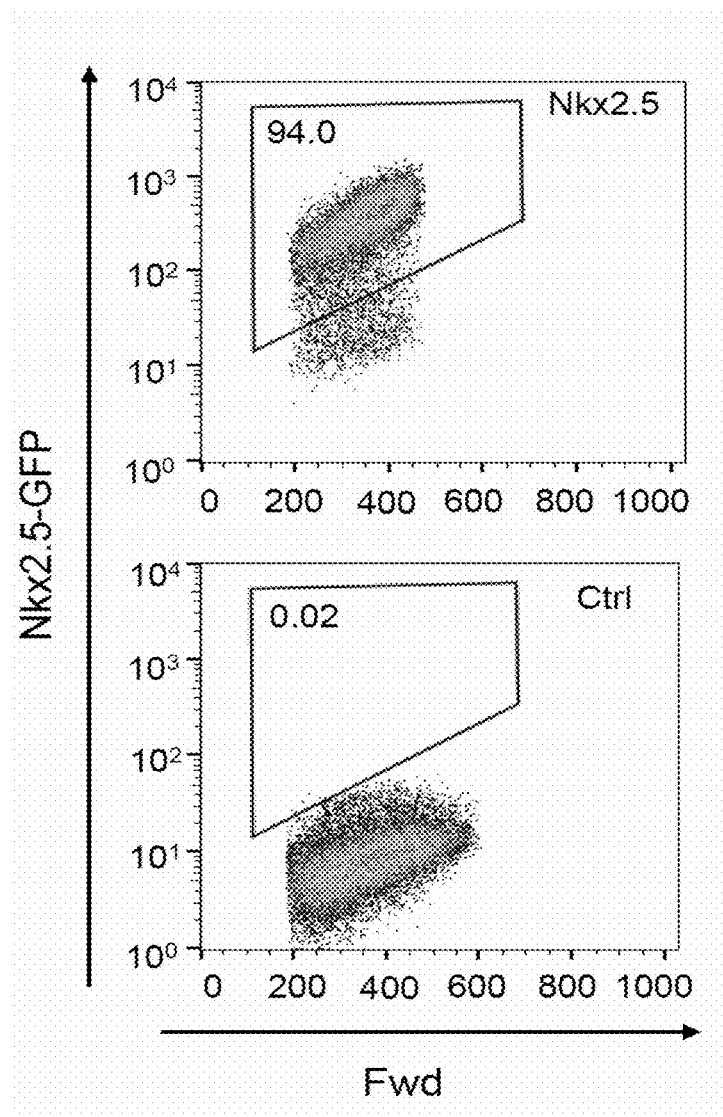
FIG. 3C shows purity of cardiomyocytes, determined by flow cytometric analysis of GFP expression, differentiated from ES03 Nkx2.5-GFP hESCs in RPMI.
Figure 4:
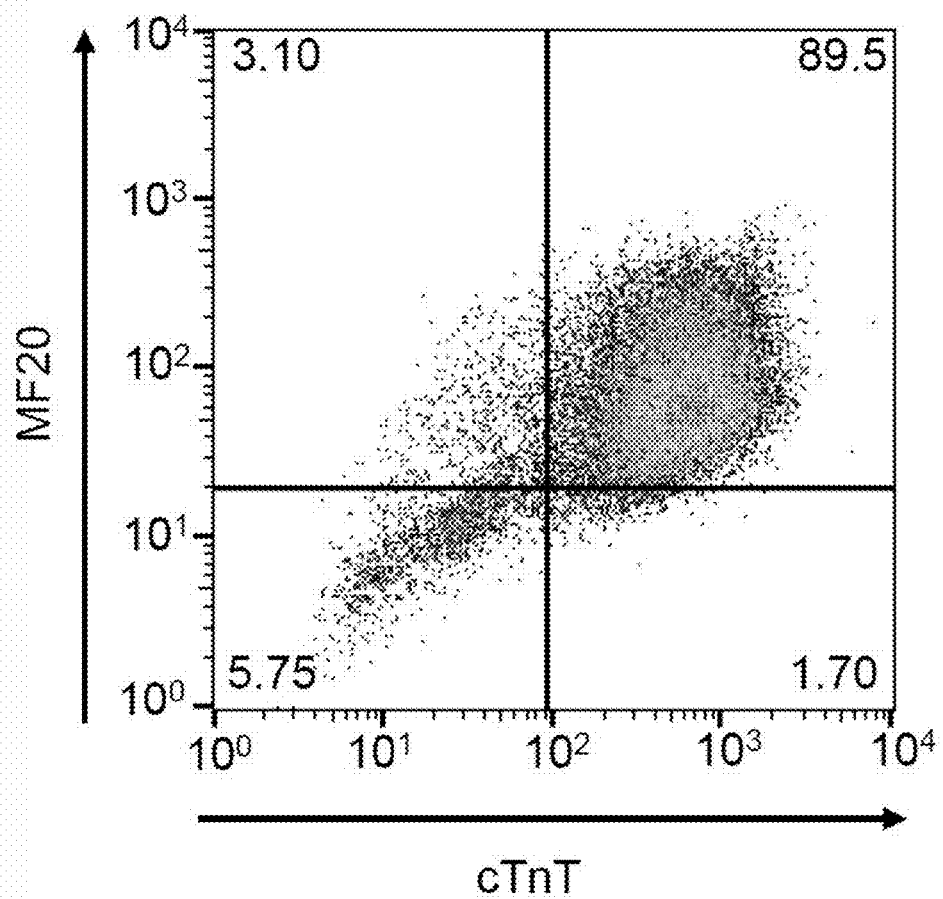
FIG. 4 shows purity of cardiomyocytes, determined by flow cytometric analysis of cTnT and sarcomeric myosin heavy chain (MF20 antibody) expression on day 15, differentiated from H1 hESCs in RPMI.
Figure 5:
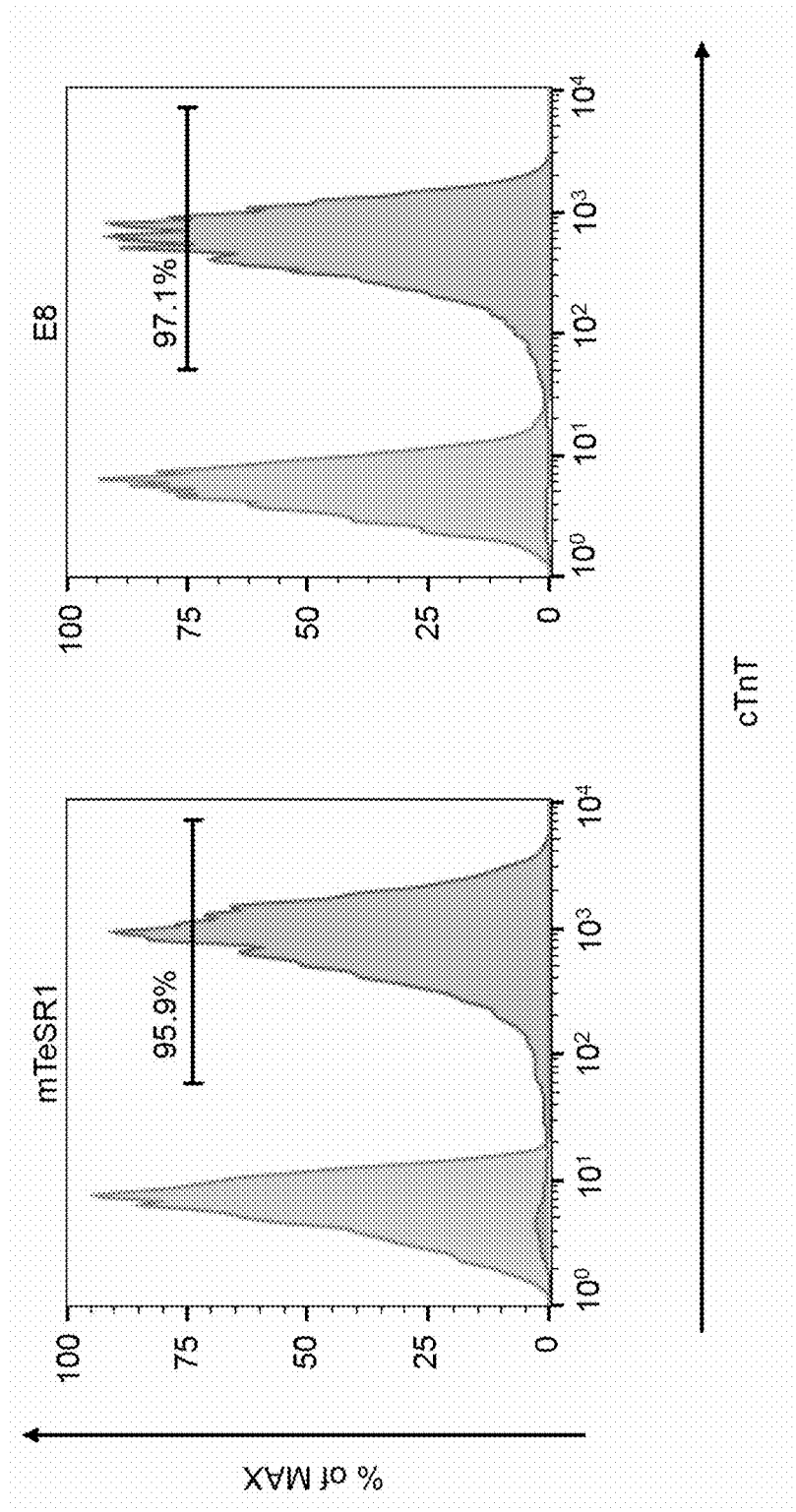
FIG. 5 shows purity of cardiomyocytes, determined by flow cytometric analysis of cTnT expression on day 15, differentiated from ES03 hESCs expanded in mTeSR1 (left panel) or E8 (right panel).

These chemically defined albumin-free conditions supported cardiac induction from hPSCs based on flow cytometry and immunostaining analysis of cTnT (FIGS. 1E and 1F), sarcomeric myosin heavy chain, α-actinin, and Nkx2.5 expression (FIGS. 3A, 3B and 3C). The albumin-free GiWi protocol also permitted more than 88% of cardiomyocyte generation from a less cardiogenic hESC line H1 (FIG. 4). In addition, our albumin-free GiWi protocol is equally effective with cells maintained in E8 or mTeSR1 (FIG. 5).

Figure 1G:
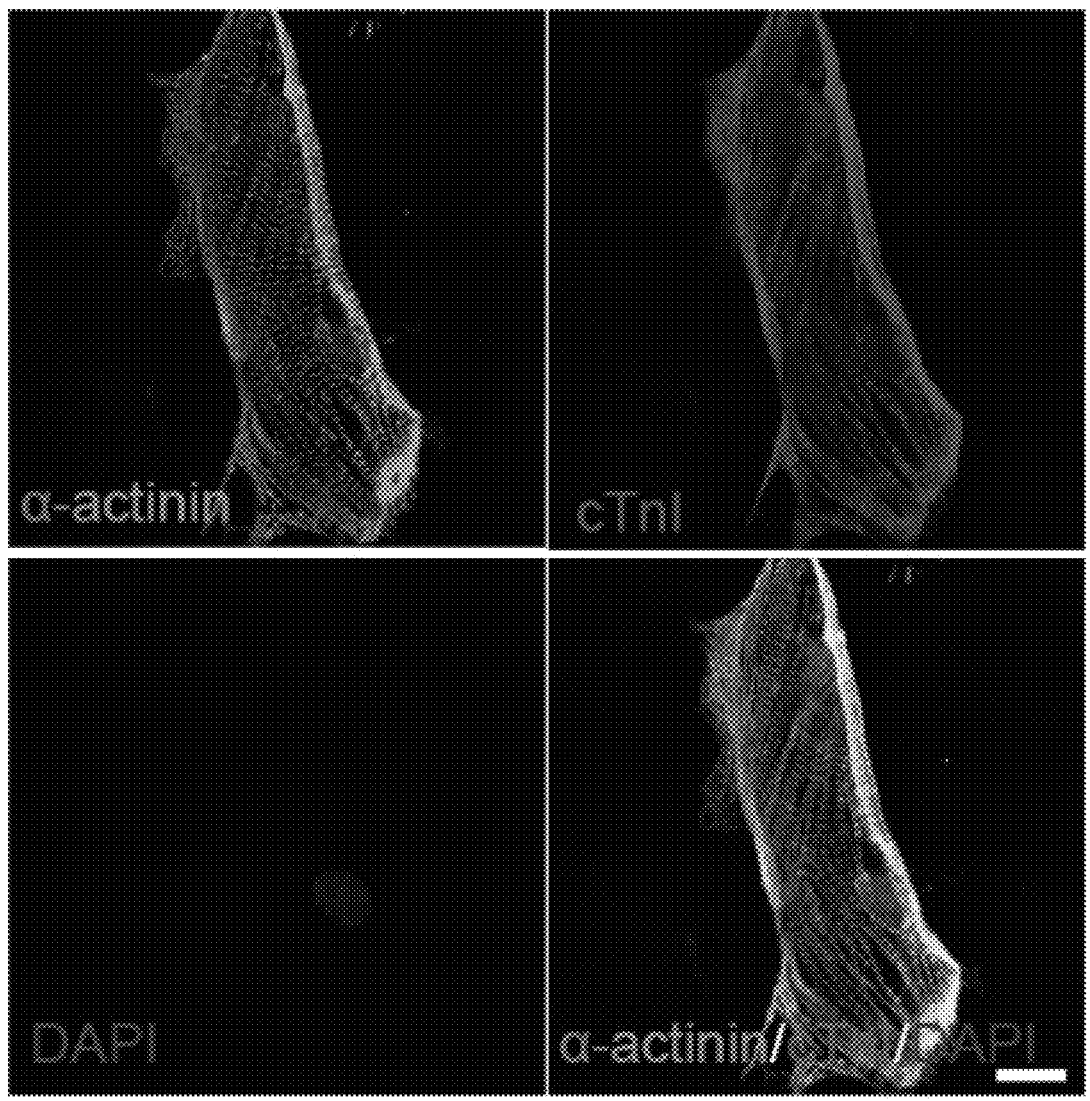
Figure 1H:
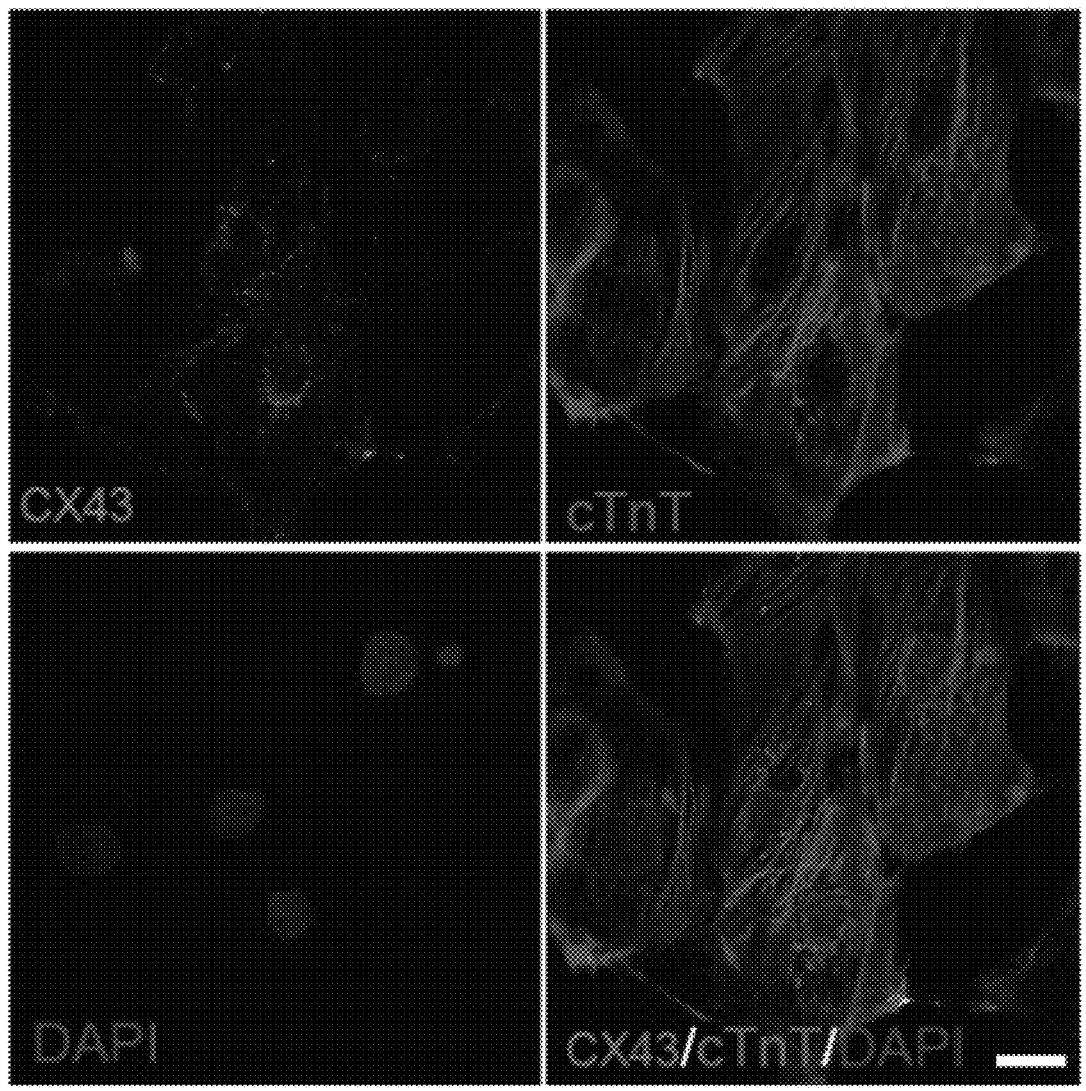
Figure 1I:
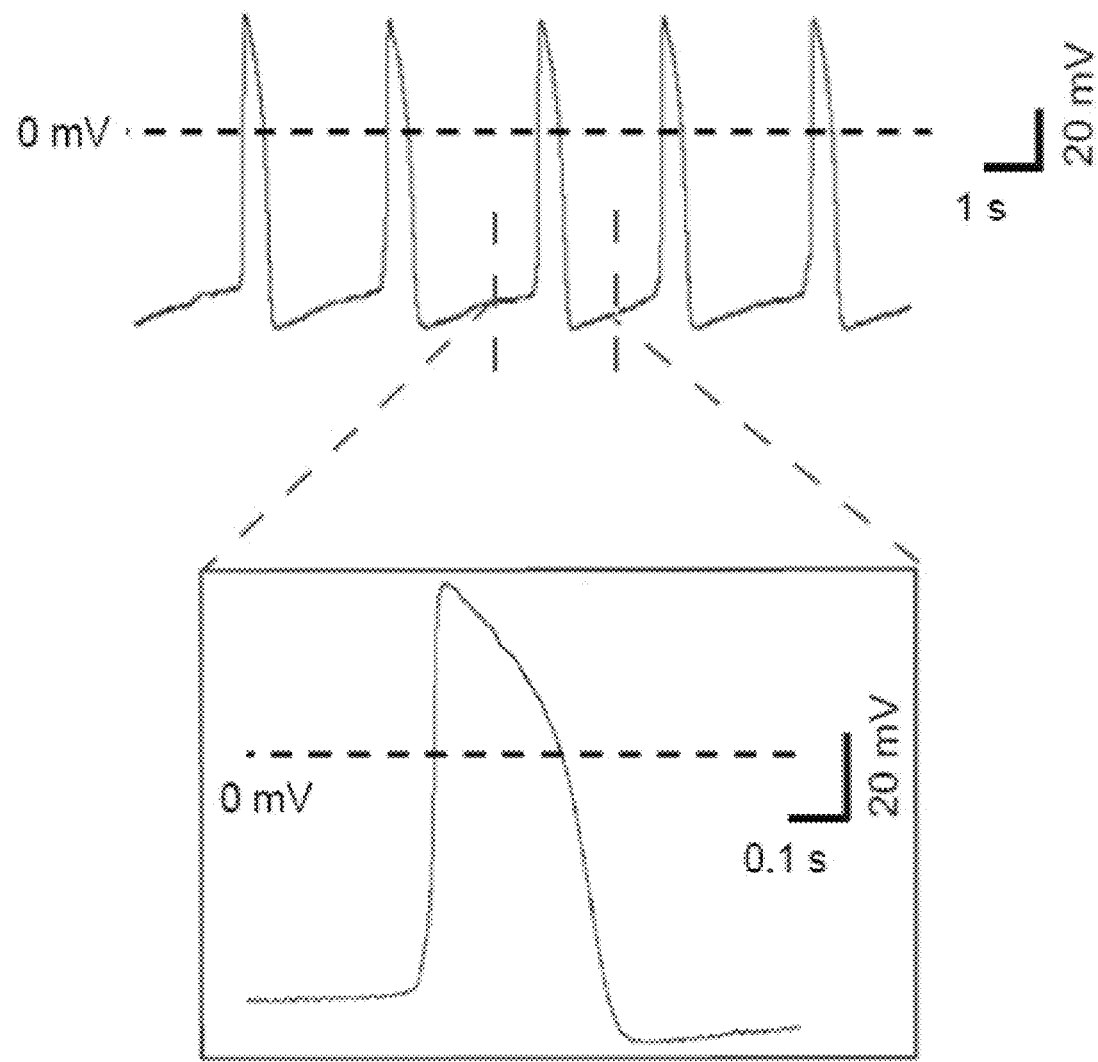

We next examined expression and localization of cardiac-specific proteins, action potential generation, and calcium flux dynamics in the resulting cardiomyocytes. The earliest wave-like spontaneous contractions in the cardiomyocytes were observed on day 7, and robust beating across the whole well was observed by day 10. The beating cells immunostained positive for cTnT and cardiac troponin I (cTnI) (FIGS. 1G and 1H). Immunostaining for α-actinin showed clear Z-line localization (FIG. 1G, Table 3), indicative of cardiac myofilament formation. The gap junction protein connexin-43 localized to cell-cell junctions (FIG. 1H). A representative recording of ventricular-like action potential is shown (FIG. 1I, Table 2).

TABLE 2

Action potential (AP) of ES03 hESC derived cardiomyocytes.

| Subtype | MDP (mV) | dV/dt$_{max}$ (V/s) | Peak (mV) | APA (mV) | APD$_{50}$ (ms) | APD$_{90}$ (ms) |
| --- | --- | --- | --- | --- | --- | --- |
| Atrial-like n = 3 | −62.0 ± 1.4 | 12.1 ± 0.7 | 36.7 ± 4.1 | 94.0 ± 3.3 | 97.8 ± 7 | 138 ± 14 |
| Ventricular-like n = 14 | −60.0 ± 2.0 | 12.0 ± 0.8 | 45.1 ± 2.1 | 97.0 ± 2.1 | 176 ± 29 | 247 ± 45 |
| Nodal-like n = 1 | −49.5 | 5.8 | 38.0 | 86.8 | 106.5 | 160.6 |

MDP, mean diastolic potential; dV/dt$_{max}$, maximal upstroke velocity; peak, the maximum voltage of the AP; APA, action potential amplitude; APD$_{50}$/APD$_{90}$, the elapsed time from the start of the action potential required to attain 50%/90% repolarization in milliseconds.
Data are presented as mean ± SEM.

As shown in Table 2, atrial, ventricular, and nodal cardiomyocytes were distinguished based on analysis of three parameters, dV/dt, APD$_{50}$, APD$_{90}$. Nodal-like cells showed dV/dt smaller than 10 V/s, while both atrial-like and ventricular-like cells showed dV/dt greater than 10 V/s. In addition, ventricular-like cells showed APD$_{50}$>100 ms and APD$_{90}$>150 ms, while atrial-like cells showed APD$_{50}$<100 ms and APD$_{90}$<150 ms.

Figure 6A:
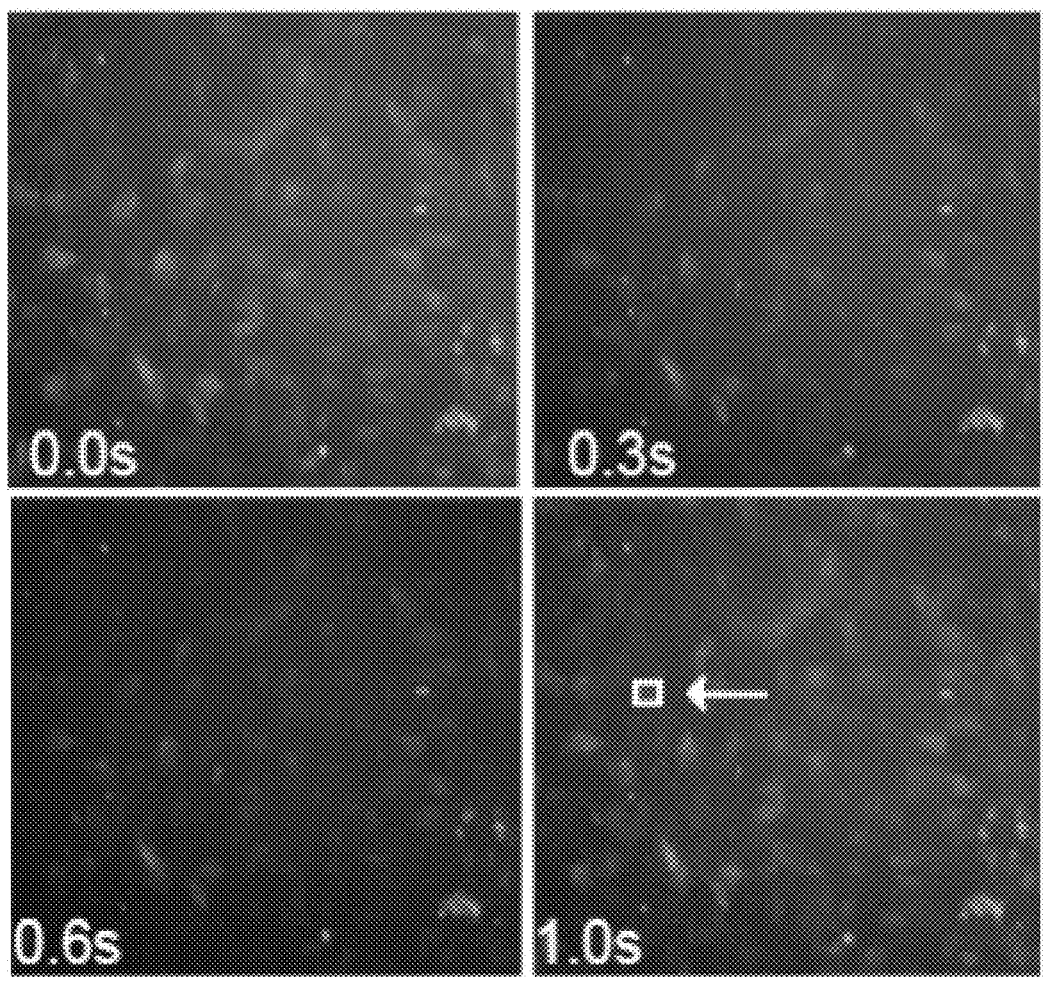
FIGS. 6A and 6B show a fluorescence analysis. Cardiomyocytes differentiated from 19-9-11 iPSCs in RPMI were treated with 10 µM Fluo-4 AM for 15 min and then $Ca^{2+}$ transients were recorded with a temporal resolution at 10 frames per second. Box (white arrow head) in FIG. 6A denotes the site of analysis of absolute fluorescence normalized to initial fluorescence (F/F0) shown in FIG. 6B.
Figure 6B:
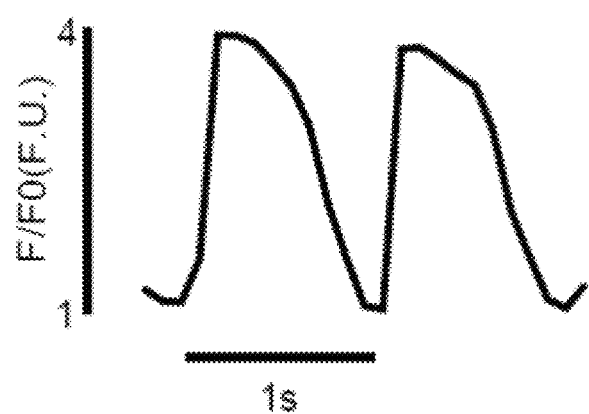
Figure 7A:
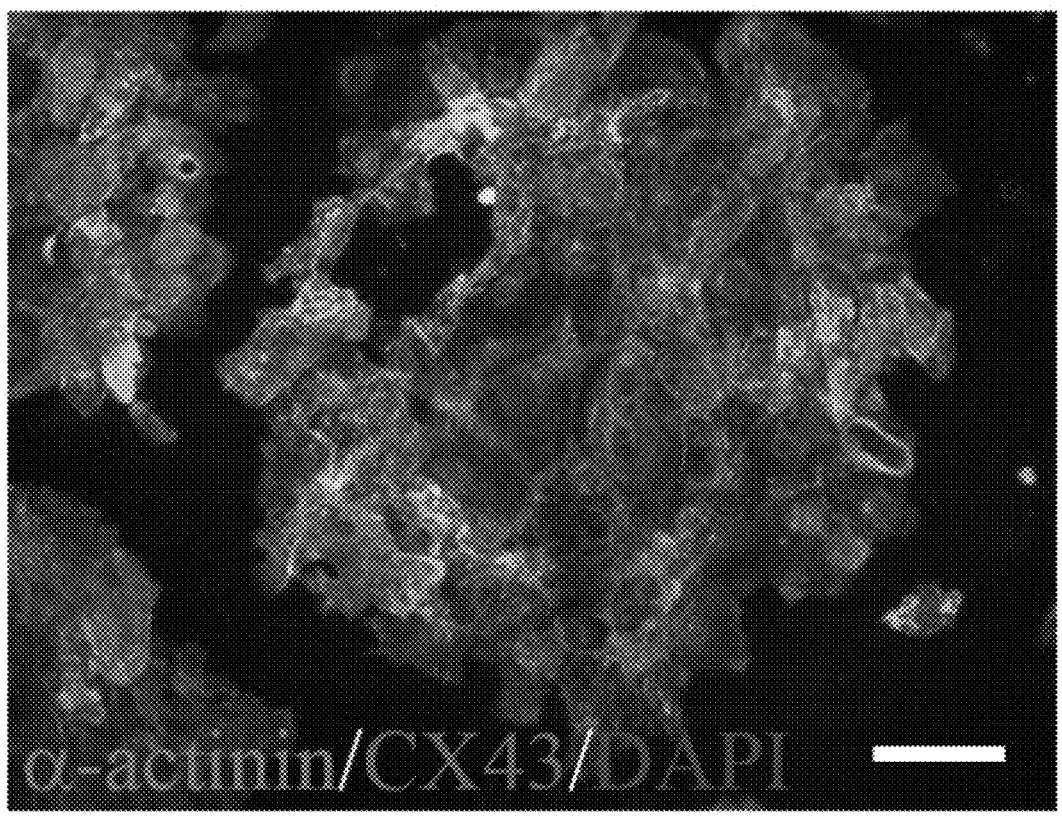
FIGS. 7A and 7B show immunolabeling of cardiomyocytes differentiated from 19-9-11iPSCs in RPMI that were cultured in CMM for 60 days.
Figure 7B:
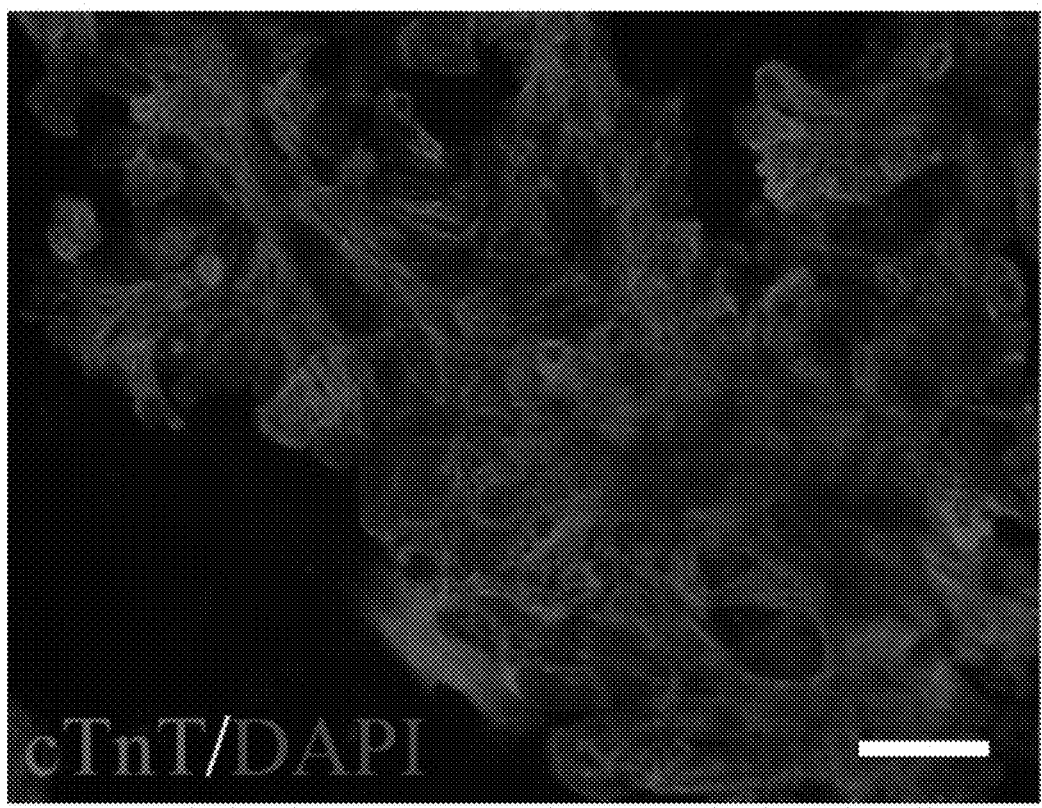

In order to assess the functional integrity and subtype of the resulting cardiomyocytes, patch clamp and dynamic Ca$^{2+}$ transient analyses were performed. Cardiomyocytes exhibited spontaneous Ca$^{2+}$ transients (FIGS. 6A and 6B), the key mechanism underlying cardiomyocyte excitation-contraction coupling. Cardiomyocytes generated using the albumin-free GiWi protocol showed immature features similar to cardiomyocytes generated in RPMI/B27-ins (Lian, X. J. et al. Robust cardiomyocyte differentiation from human pluripotent stem cells via temporal modulation of canonical Wnt signaling. Proc. Natl. Acad. Sci. U.S.A 109, E1848-57 (2012)). After long-term culture (60 days) of cardiomyocytes in albumin-free medium, immunostaining experiments showed that cardiomyocytes generated using albumin-free protocol are positive for cTnT, α-actinin and connexin-43 (FIGS. 7A and 7B).

Taken together, these results demonstrate that the GiWi protocol in RPMI lacking supplements generates high purity populations of functional cardiomyocytes. This albumin-free protocol generated 10$^6$ cardiomyocytes/cm$^2$ at more than 90% purity, similar to or exceeding cardiomyocyte production in the presence of albumin (Lian, X. et al. Robust cardiomyocyte differentiation from human pluripotent stem cells via temporal modulation of canonical Wnt signaling. Proc. Natl. Acad. Sci. U.S.A. 109, E1848-E1857 (2012); Burridge, P. W. et al. Chemically defined generation of human cardiomyocytes. Nat. Methods 11, 855-860 (2014)).

Differences between our study and the Burridge et al. report (Chemically defined generation of human cardiomyocytes. Nat. Methods 11, 855-860 (2014)), including the initial cell density at initiation of differentiation and the exposure time windows for GiWi chemicals, may account for their finding that albumin is necessary for cardiomyocyte differentiation. For example, we reported an optimum application of Gsk3 inhibitor from days 0-1 and Wnt inhibitor from days 3-5 while Burridge et al. applied the Gsk3 inhibitor from days 0-2 and the Wnt inhibitor from days 2-4. We also found that treatment of hPSCs with the same concentration of CH as Burridge et al. used for 2 days in albumin-free medium caused substantial cell death. However, reducing the CH concentration and/or treatment time in the absence of albumin permits efficient mesendoderm induction without cytotoxicity.

In sum, this Example demonstrates that mesoderm differentiation induced by Gsk3 inhibitor is more efficient in the absence of albumin, and discloses an efficient, robust, and defined cardiomyocyte differentiation protocol in the absence of albumin. This albumin-free protocol is simpler and more cost-effective than existing cardiomyocyte differentiation platforms, and will facilitate large scale production of human cardiomyocytes for suitable for research and therapeutic applications.

Example 2: Detailed Materials and Methods for Example 1

In this Example, we provide a detailed description of the materials and methods used in the studies described in Example 1 above.

Methods.

Maintenance of hPSCs. hESCs (ES03, H1, H9 (Thomson, J. A. et al Embryonic stem cell lines derived from human blastocysts. *Science* 282, 1145-7 (1998)), HS181 (Ström, S. et al. Derivation of 30 human embryonic stem cell lines-improving the quality. *In Vitro Cell. Dev. Biol. Anim.* 46, 337-44 (2010))) and human iPSCs (19-9-7 (Yu, J. et al. Human induced pluripotent stem cells free of vector and transgene sequences. *Science* 324, 797-801 (2009)), 19-9-11 (Yu, J. et at Human induced pluripotent stem cells free of vector and transgene sequences. *Science* 324, 797-801 (2009)), 6-9-9 (Yu, J. et al. Human induced pluripotent stem cells free of vector and transgene sequences. *Science* 324, 797-801 (2009)), IMR90C4 (Yu, J. et al. Induced pluripotent stem cell lines derived from human somatic cells. *Science* 318, 1917-20 (2007))) were maintained on Synthemax coated plates (Corning) (Melkoumian, Z. et al. Synthetic peptide-acrylate surfaces for long-term self-renewal and cardiomyocyte differentiation of human embryonic stem cells. *Nat. Biotechnol.* 28, 606-10 (2010)) in E8 medium (Chen, G. et al. Chemically defined conditions for human iPSC derivation and culture. *Nat. Methods* 8, 424-9 (2011)). ES03-GFP line was generated by nucleofection of ES03 cells with PB—UBC-GFP-PGK-neo and pCyL43 plasmids (Wang, W. et al. Chromosomal transposition of PiggyBac in mouse embryonic stem cells. *Proc. Natl. Acad. Sci. U.S.A.* 105, 9290-5 (2008)) followed by 200 µg/ml G418 selection for two weeks.

Cardiac Differentiation Via GiWi Protocol Using RPMI Differentiation Medium.

hPSCs maintained on a Synthemax-coated surface in E8 or mTeSR1 medium were dissociated into single cells with Accutase® (Life Technologies) at 37° C. for 5 min and then seeded onto a Synthemax-coated cell culture dish at 100,000-200,000 cell/cm$^2$ in E8 supplemented with 5 µM ROCK inhibitor Y-27632 (Selleckchem)(day −2) for 24 hours. Cells were then cultured in E8, changed daily. At day 0, cells were treated with 6 µM CH1R99021 (Selleckchem) in RPMI medium for 24 hours (day 0 to day 1). At day 0 the cell density should be between 250,000 and 400,000 cells/cm$^2$. At day 3, half the medium was changed to fresh RPMI medium containing 2.5 µM IWP2 (Tocris). At day 5, the entire medium was changed with RPMI medium. Cells were maintained in the cardiomyocyte maintenance medium (CMM: RPMI supplemented with 10 µg/ml insulin (sigma) and 200 µg/ml L-Ascorbic acid 2-phosphate sesquimagnesium salt hydrate (sigma)) starting from day 7, with the medium changed every 2 days.

Flow Cytometry.

Cells were dissociated into single cells with Accutase® for 10 min and then fixed with 1% paraformaldehyde for 20 min at room temperature and stained with primary and secondary antibodies (Table 3) in PBS plus 0.1% Triton X-100 and 0.5% BSA. Data were collected on a FACSCaliber flow cytometer (Beckton Dickinson) and analyzed using FlowJo.

TABLE 3

Antibodies used in this study.

| Antibody | Isotype/source/cat. no./clone | Concentration |
| --- | --- | --- |
| Cardiac troponin T | Mouse IgG1/Lab Vision/ms295-p1-13-11 | 1:200 |
| Cardiac troponin I | Rabbit IgG/Santa Cruz/sc-15368/H-170 | 1:100 |
| MLC2a | Mouse IgG2b/Synaptic systems/311011/56F5 | 1:200 |
| α-Actinin | Mouse IgG1/Sigma-Aldrich/A7811/EA-53 | 1:500 |
| Brachyury | Goat polyclonal IgG/R&D Systems/AF2085 | 1:100 |
| Connexin 43 | Rabbit IgG/Cell Signaling Tech/3512S | 1:200 |
| β-Actin | Rabbit mAb (HRP conjugate)/Cell Signaling Tech/13E5/5125S | 1:1,000 (WB) |
| Secondary Antibody | Alexa 488 Chicken anti-Gt IgG/A-21467 | 1:1,000 |
| Secondary Antibody | Alexa 488 Goat anti-Ms IgG1/A-21121 | 1:1,000 |
| Secondary Antibody | Alexa 488 Goat anti-RbIgG/A-11008 | 1:1,000 |
| Secondary Antibody | Alexa 594 Goat anti-Ms IgG2b/A-21145 | 1:1,000 |
| Secondary Antibody | Alexa 594 Goat anti-RbIgG/A-11012 | 1:1,000 |
| Secondary Antibody | Alexa 647 Goat anti-Ms IgG2b/A-21242 | 1:1,000 |
| Secondary Antibody | Alexa 647 Goat anti-RbIgG/A-21244 | 1:1,000 |
| Secondary Antibody | Donkey anti-Gt IgG (HRP conjugated)/Santa Cruz/sc-2020 | 1:5,000 (WB) |

Immunostaining.

Cells were fixed with 4% paraformaldehyde for 15 min at room temperature and then stained with primary and secondary antibodies (Table 3) in PBS plus 0.4% Triton X-100 and 5% non-fat dry milk (Bio-Rad). Nuclei were stained with Gold Anti-fade Reagent with DAPI (Invitrogen). An epifluorescence microscope (Leica DM IRB) with a QImaging® Retiga 4000R camera was used for imaging analysis.

Western Blot Analysis.

Cells were lysed in M-PER Mammalian Protein Extraction Reagent (Pierce) in the presence of Halt Protease and Phosphatase Inhibitor Cocktail (Pierce). Proteins were separated by 10% Tris-Glycine SDS/PAGE (Invitrogen) under denaturing conditions and transferred to a nitrocellulose membrane. After blocking with 5% dried milk in TBST, the membrane was incubated with primary antibody overnight at 4° C. The membrane was then washed, incubated with an anti-mouse/rabbit peroxidase-conjugated secondary antibody (Table 3) at room temperature for 1 hour, and developed by SuperSignal chemiluminescence (Pierce).

Electrophysiology (Patch Clamping).

Beating cardiomyocyte clusters were microdissected and replated onto glass coverslips or coverslip dishes (MatTek, P35G-0-14-C) and were maintained in cardiomyocyte maintenance medium before recording. Action potential activity was assessed using borosilicate glass pipettes (4-5 MOhm resistance) filled with intracellular solution consisting of 120 mM K D-gluconate, 25 mM KCl, 4 mM MgATP, 2 mM NaGTP, 4 mM $Na_2$-phospho-creatin, 10 mM EGTA, 1 mM $CaCl_2$, and 10 mM HEPES (pH 7.4 adjusted with HCl at 25° C.). Cultured cardiomyocytes seeded on coverslip dishes were submerged in extracellular solution (Tyrode's solution) containing 140 mM NaCl, 5.4 mM KCl, 1 mM $MgCl_2$, 10 mM glucose, 1.8 mM $CaCl_2$, and 10 mM HEPES (pH 7.4 adjusted with NaOH at 25° C.). Spontaneous action potentials were recorded at 37° C. using patch clamp technique (whole-cell, current clamp configuration) performed using a Multiclamp 700B amplifier (Molecular Devices, CA, USA) software low-pass filtered at 1 kHz, digitized and stored using a Digidata 1322A and Clampex 9.6 software (Molecular Devices, CA, USA).

Intracellular $Ca^{2+}$ Transient Assay in hPSC-Derived Cardiomyocytes.

Cardiomyocytes derived from hPSCs were treated with 10 µM Fluo-4 AM (Life Technologies, F14217) in CMM for 15 min at 37° C. in a 5% $CO_2$ incubator. After this, cells were washed with PBS twice and then fed with pre-warmed CMM. Cells were incubated in 37° C., 5% $CO_2$ for another 30 min prior to imaging. Calcium transients of single cardiomyocyte were then recorded with a temporal resolution of 10 frames per second. The data were then quantified as the background subtracted fluorescence intensity changes normalized to the background-subtracted baseline fluorescence in Fiji.

Statistics.

Data are presented as mean±standard error of the mean (SEM) or standard derivation (SD). Statistical significance was determined by Student's t-test (two-tail) between two groups. P<0.05 was considered statistically significant.

Example 3: Inhibiting Signaling Immediately after Activating Signaling

In this Example, we demonstrate that the step of inhibiting Wnt/β-catenin signaling may be performed immediately after the step of activating Wnt/β-catenin signaling. No intervening "rest" period, during which no Wnt/β-catenin signaling activation or inhibition takes place, is required to successfully differentiate cardiomyocytes using the disclosed protocol.

Figure 8:
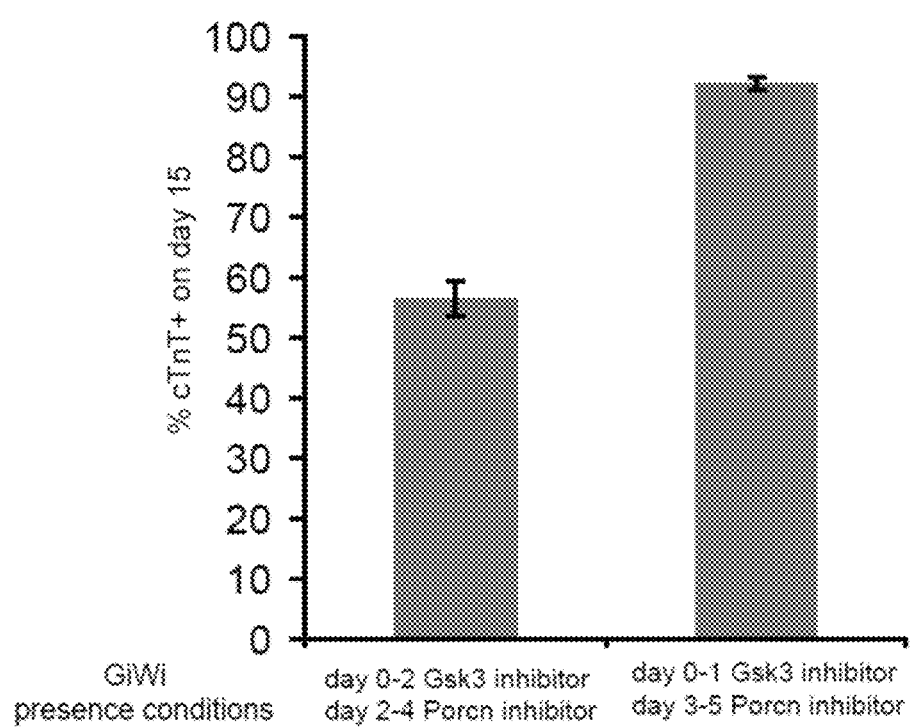
FIG. 8 shows cardiomyocyte purity (as determined by flow cytometry analysis of cTnT expression on day 15) for cells derived from hPSCs in albumin-free media using a GiWi protocol with (right column) or without (left column) an intervening "rest" period between Gsk inhibition by CH and porcupine inhibition by IWP2.

Referring to FIG. 8, the right column shows cardiomyocyte differentiation (as determined by flow cytometry analysis of cTnT expression on day 15) for cells derived from hPSCs in albumin-free media using the GiWi protocol outlined in Examples 1 and 2, using the timeline shown in FIG. 1A. Specifically this protocol included an intervening "rest" period between Gsk inhibition by CH, which occurred on days 0-1, and porcupine inhibition by IWP2, which occurred on days 3-5. During the intervening "rest" period (days 1-3), cells were cultured in the basal medium in the absence of a Gsk or porcupine inhibitor.

The left column shows successful cardiomyocyte differentiation for cells derived from hPSCs in albumin-free media using a similar GiWi protocol, except that the protocol did not include an intervening "rest" period between Gsk inhibition by CH, which occurred on days 0-2, and porcupine inhibition by IWP2, which occurred on days 2-4. These results show that the intervening "rest" period is not necessary to facilitate successful GiWi-based cardiomyocyte differentiation of hPSCs in albumin-free media.

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

The invention claimed is:

1. A method for generating a population of cardiomyocyte progenitors from human pluripotent stem cells, comprising:
   (i) activating Wnt/β-catenin signaling in human pluripotent stem cells by culturing the human pluripotent stem cells in the presence of a Gsk3 inhibitor to obtain a first cell population; and
   (ii) subsequently inhibiting Wnt/β-catenin signaling in the first cell population while culturing the first cell population to obtain a second cell population comprising human cardiomyocyte progenitors,
   wherein the first cell population in step (ii) is cultured under albumin-free conditions.

2. The method of claim 1, wherein the Gsk3 inhibitor is a small molecule selected from the group consisting of CHIR 99021, CHIR 98014, BIO-acetoxime, BIO, LiCl, SB 216763, SB 415286, AR A014418, 1-Azakenpaullone, and Bis-7-indolylmaleimide.

3. The method of claim 2, wherein the small molecule Gsk3 inhibitor is selected from the group consisting of CHIR 99021, CHIR 98014, and BIO-acetoxime.

4. The method of claim 2, wherein in step (i), the small molecule Gsk3 inhibitor is present in a concentration of from 0.2 to 9 μM.

5. The method of claim 1, wherein the step of inhibiting the Wnt/β-catenin signaling in the first cell population comprises contacting the first cell population with a small molecule that inhibits Wnt/β-catenin signaling.

6. The method of claim 5, wherein the small molecule that inhibits Wnt/β-catenin signaling stabilizes axin and stimulates β-catenin degradation.

7. The method of claim 6, wherein the small molecule that stimulates β-catenin degradation and stabilizes axin is XAV939 or IWR-1.

8. The method of claim 5, wherein the small molecule that inhibits Wnt/β-catenin signaling is a porcupine inhibitor that prevents palmitylation of Wnt proteins by porcupine.

9. The method of claim 8, wherein the porcupine inhibitor is IWP2, IWP4, or a combination thereof.

10. The method of claim 9, wherein in step (ii), the porcupine inhibitor is present in a concentration of from 1 to 4 μM.

11. The method of claim 1, wherein the step of inhibiting the Wnt/β-catenin signaling in the first cell population comprises contacting the first cell population with at least one antibody that blocks activation of a Wnt ligand receptor.

12. The method of claim 11, wherein the at least one antibody binds to one or more Wnt ligand family members.

13. The method of claim 1, wherein the step of inhibiting the Wnt/β-catenin signaling in the first cell population comprises reducing β-catenin expression in the first cell population.

14. The method of claim 13, wherein reducing β-catenin expression comprises expressing shRNA for β-catenin in the first cell population.

15. The method of claim 1, wherein the pluripotent stem cells in step (i), the first cell population in step (ii), or both are cultured under conditions that are free of one or more of the group consisting of L-ascorbic acid 2-phosphate, transferrin, sodium selenite, progesterone, and putrescine.

16. The method of claim 1, wherein step (ii) of inhibiting Wnt/β-catenin signaling in the first cell population is performed immediately after step (i) of activating Wnt/β-catenin signaling in the human pluripotent stem cells is completed.

17. The method of claim 1, further comprising culturing the second cell population after ending the inhibition of Wnt/β-catenin signaling initiated during step (ii) to obtain a cell population comprising cardiomyocytes.

18. The method of claim 17, wherein no cell separation or selection step is used to obtain the cell population comprising cardiomyocytes.

19. The method of claim 18, wherein at least 85% of the cells in the cell population comprising cardiomyocytes are cardiac troponin T (cTnT)-positive.

20. A method for culturing pluripotent stem cells to obtain a population of cardiomyocytes, the method comprising the steps of:
   sequentially inhibiting Gsk3 in the pluripotent cells and then inhibiting Wnt signaling in the Gsk3 inhibited cells under albumin-free conditions; and
   culturing the sequentially inhibited cells in an albumin-free culture medium to form a differentiated cell population comprising cardiomyocytes.

* * * * *

UNITED STATES PATENT AND TRADEMARK OFFICE
CERTIFICATE OF CORRECTION

PATENT NO.        : 9,765,299 B2
APPLICATION NO.   : 14/850451
DATED             : September 19, 2017
INVENTOR(S)       : Palecek, Lian and Bao Page 1 of 1

It is certified that error appears in the above-identified patent and that said Letters Patent is hereby corrected as shown below:

Column 7, Line 25 - "TGF" should be --TGβ--.

Column 9, Line 55 - "alphα-actinin" should be --alpha-actinin--.

Column 11, Line 39 - "LRPS/" should be --LRP5/--.

Column 11, Line 57 - "Wnt-059" should be --Wnt-C59--.

Column 12, Line 32 - "Wnt-059" should be --Wnt-C59--.

Signed and Sealed this
Twelfth Day of December, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 2

<210> SEQ ID NO 1
<211> LENGTH: 57
<212> TYPE: DNA
<213> ORGANISM: Artificial Sequence
<220> FEATURE:
<223> OTHER INFORMATION: Synthetic short hairpin interfering nucleic
      acid sequence

<400> SEQUENCE: 1
ccggaggtgc tatctgtctg ctctactcga gtagagcaga cagatagcac ctttttt      57

<210> SEQ ID NO 2
<211> LENGTH: 57
<212> TYPE: DNA
<213> ORGANISM: Artificial Sequence
<220> FEATURE:
<223> OTHER INFORMATION: Synthetic short interfering nucleic acid
      sequence

<400> SEQUENCE: 2
ccgggcttgg aatgagactg ctgatctcga gatcagcagt ctcattccaa gctttttt     57
```